US008563145B2

(12) United States Patent
Iwakuma et al.

(10) Patent No.: US 8,563,145 B2
(45) Date of Patent: Oct. 22, 2013

(54) MATERIAL CONTAINING TWO OR THREE DIBENZOFURAN GROUPS, DIBENZOTHIOPHENE GROUPS, OR A COMBINATION THEREOF, WHICH IS OPERABLE FOR ORGANIC ELECTROLUMINESCENCE ELEMENTS, AND ORGANIC ELECTROLUMINESCENCE ELEMENTS USING THE MATERIAL

(75) Inventors: Toshihiro Iwakuma, Chiba (JP); Masahide Matsuura, Chiba (JP); Yuki Nakano, Chiba (JP); Hidetsugu Ikeda, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 301 days.

(21) Appl. No.: 12/303,199

(22) PCT Filed: May 29, 2007

(86) PCT No.: PCT/JP2007/060921
§ 371 (c)(1), (2), (4) Date: Jan. 14, 2009

(87) PCT Pub. No.: WO2007/142083
PCT Pub. Date: Dec. 13, 2007

(65) Prior Publication Data
US 2009/0224658 A1 Sep. 10, 2009

(30) Foreign Application Priority Data

Jun. 2, 2006 (JP) ................................. 2006-154305

(51) Int. Cl.
*H01L 51/54* (2006.01)
*C09K 11/06* (2006.01)

(52) U.S. Cl.
USPC ........... 428/690; 428/917; 313/502; 313/504; 549/4; 549/219; 556/489

(58) Field of Classification Search
None
See application file for complete search history.

(56) References Cited

U.S. PATENT DOCUMENTS

| 4,513,137 | A | 4/1985 | Koser et al. | |
|---|---|---|---|---|
| 6,310,231 | B1 | 10/2001 | Igarashi et al. | |
| 7,651,791 | B2 * | 1/2010 | Nakano et al. | 428/690 |
| 2003/0181694 | A1 | 9/2003 | Shirane et al. | |
| 2004/0209115 | A1 | 10/2004 | Thompson et al. | |
| 2005/0064238 | A1 | 3/2005 | Lee et al. | |
| 2005/0067951 | A1 | 3/2005 | Richter et al. | |
| 2005/0164032 | A1 | 7/2005 | Ise et al. | |
| 2005/0238919 | A1 | 10/2005 | Ogasawara | |
| 2005/0238920 | A1 | 10/2005 | Sotoyama et al. | |
| 2005/0260441 | A1 * | 11/2005 | Thompson et al. | 428/690 |
| 2006/0051613 | A1 * | 3/2006 | Tomita et al. | 428/690 |
| 2007/0063190 | A1 * | 3/2007 | Kobayashi et al. | 257/40 |
| 2007/0247063 | A1 * | 10/2007 | Murase et al. | 313/504 |

FOREIGN PATENT DOCUMENTS

| CN | 1462483 A | 12/2003 |
|---|---|---|
| CN | 1654496 A | 8/2005 |
| EP | 2 001 064 A1 | 12/2008 |
| JP | 3-200889 | 9/1991 |
| JP | 5-109485 | 4/1993 |
| JP | 7-138561 | 5/1995 |
| JP | 8-239655 | 9/1996 |
| JP | 2002-308837 | 10/2002 |
| JP | 2003-138251 | 5/2003 |
| JP | 2004-2351 | 1/2004 |
| JP | 2004-103463 | 4/2004 |
| JP | 2004-200104 | 7/2004 |
| JP | 2004253298 A * | 9/2004 |
| JP | 2005-97301 | 4/2005 |
| JP | 2005-306864 | 11/2005 |
| JP | 2005-317275 | 11/2005 |
| WO | WO 97/46547 | 12/1997 |
| WO | WO 03/059015 A1 | 7/2003 |
| WO | WO 2004/096945 A1 | 11/2004 |
| WO | WO 2005033090 A1 * | 4/2005 |
| WO | WO 2005/101912 A1 | 10/2005 |
| WO | WO 2005113531 A1 * | 12/2005 |
| WO | WO 2006128800 A1 * | 12/2006 |

OTHER PUBLICATIONS

Gilman et al. J. Am. Chem. Soc. 1950, 72, 2629-2632. Date of publication: Jun. 1950.*
Machine translation of JP2004-002351. Date of publication: Jan. 8, 2004.*
Machine translation of JP2004-103463. Date of publication: Apr. 2, 2004.*
Machine translation of JP2004-253298. Date of publication: Sep. 9, 2004.*
U.S. Appl. No. 12/632,988, filed Dec. 8, 2009, Nakano, et al.
M. A. Baldo, et al., "Very High-Efficiency Green Organic Light-Emitting Devices Based on Electrophosphorescence", Applied Physics Letters, vol. 75. No. 1 Jul. 5, 1999, 3 pages.
D. F. O'Brien, et al., "Improved Energy Transfer in Electrophosphorescent Devices", Applied Physics Letters, vol. 74, No. 3, Jan. 18, 1999, 3 pages.
Extended European Search Report issued Nov. 30, 2010, in Application No. / Patent No. 07744340.6-1235 / 2034538 PCT/JP2007060921.
Jun-ichi Yoshida, et al., "Electrochemical Synthesis of Organosilicon Compounds", J. Org. Chem. vol. 51, XP-002609580, Oct. 1986, pp. 3996-4000.
Mitsuo Ishikawa, et al., "The Chemistry of Siloles Synthesis and Reactions of $\eta^6$-[1-Methyl-1-(Trimethylsilyl)Dibenzosilacyclopentadien Chromium Tricarbonyl", Journal of Organometallic Chemistry, vol. 271, XP-002609581, Aug. 21, 1984, pp. C4-C6.

* cited by examiner

*Primary Examiner* — Gerard Higgins
*Assistant Examiner* — Andrew K Bohaty
(74) *Attorney, Agent, or Firm* — Oblon, Spivak, McClelland, Maier & Neustadt, L.L.P.

(57) ABSTRACT

An organic electroluminescence device comprising a compound having a specific structure having a heteroatom and an organic electroluminescence device which comprises a cathode, an anode and an organic thin film layer which comprises at least one layer comprising at least a light emitting layer and is disposed between the cathode and the anode, wherein at least one layer in the organic thin film layer comprises the above compound. The device provides excellent efficiency of light emission, forms no defects in pixels, exhibits excellent heat resistance and has a long life.

19 Claims, No Drawings

MATERIAL CONTAINING TWO OR THREE DIBENZOFURAN GROUPS, DIBENZOTHIOPHENE GROUPS, OR A COMBINATION THEREOF, WHICH IS OPERABLE FOR ORGANIC ELECTROLUMINESCENCE ELEMENTS, AND ORGANIC ELECTROLUMINESCENCE ELEMENTS USING THE MATERIAL

CROSS REFERENCE TO RELATED APPLICATION

This application is a 371 of PCT/JP07/060921, filed on May 29, 2007, and claims priority to Japanese Patent Application No. 2006-154305, filed on Jun. 2, 2006.

TECHNICAL FIELD

The present invention relates to a material for organic electroluminescence devices and an organic electroluminescence device using the material and, more particularly, to an organic electroluminescence device providing excellent efficiency of light emission, forming no defects in pixels, exhibiting excellent heat resistance and having a long life and a material for organic electroluminescence devices which enables to obtain the device.

BACKGROUND ART

An organic electroluminescence (hereinafter, "electroluminescence" will be referred to as "EL", occasionally) device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used tris(8-hydroxyquinolinolato)aluminum for the light emitting layer and a triphenyldiamine derivative for the hole transporting layer. Advantages of the laminate structure are that the efficiency of hole injection into the light emitting layer can be increased, that the efficiency of forming excited particles which are formed by blocking and recombining electrons injected from the cathode can be increased, and that excited particles formed within the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

As the light emitting material, chelate complexes such as tris(8-quinolinolato)aluminum complex, coumarin derivatives, tetraphenylbutadiene derivatives, distyrylarylene derivatives and oxadiazole derivatives are known. It is reported that light in the visible region ranging from blue light to red light can be obtained by using these light emitting materials, and development of a device exhibiting color images is expected (for example, refer to Patent References 1 to 3). It is recently proposed that an organic phosphorescent material other than the fluorescent material is used in the light emitting layer of an organic EL device (for example, refer to Non-Patent Reference 1 and Non-Patent Reference 2). As described above, a great efficiency of light emission is achieved by utilizing an organic phosphorescent material excited to the singlet state and the triplet state in the light emitting layer of an organic EL device. It is considered that singlet excimers and triplet excimers are formed in relative amounts of 1:3 due to the difference in the multiplicity of spin when electrons and holes are recombined in an organic EL device. Therefore, it is expected that an efficiency of light emission 3 to 4 times as great as that of a device utilizing fluorescence alone can be achieved by utilizing a material emitting phosphorescent light.

In the organic EL devices described above, a construction formed by successively laminating layers such as an anode, a hole transporting layer, an organic light emitting layer, an electron transporting layer (a hole barrier layer), an electron transporting layer and a cathode is used so that the excited state of the triplet or excimers of the triplet do not fail to emit light, and a host compound and a phosphorescent compound are used for the organic light emitting layer (for example, Patent References 4 to 8). In these patent references, host materials having a skeleton structure of dibenzofuran or dibenzothiophene are described. However, it is not described whether a device using the above host material exhibits more excellent performance than devices using other materials having the carbazolyl skeleton structure. No descriptions can be found on combinations having silicon atom or germanium atom, either.

In Patent Reference 9 and 10, compounds having substituents such as arylsilyl groups are described. However, the compounds described in the present invention are not described. Moreover, no descriptions are found on the useful effect as the material for organic EL devices, in particular, as the phosphorescent material for organic EL devices emitting bluish light, such as the effect that the energy gap of the triplet state can be kept broad.

In Patent Reference 11 to 18, arylsilane-based compounds and arylgermane-based compounds are described, and the use of these compounds as the host material for a phosphorescent device emitting bluish light is described in the examples. However, the compounds described in the present invention are not described, and the effects of the compounds are not known.

[Patent Reference 1] Japanese Patent Application Laid-Open No. Heisei 8 (1996)-239655
[Patent Reference 2] Japanese Patent Application Laid-Open No. Heisei 7 (1995)-138561
[Patent Reference 3] Japanese Patent Application Laid-Open No. Heisei 3 (1991)-200889
[Patent Reference 4] International Patent Application Laid-Open No. WO05/101912
[Patent Reference 5] Japanese Patent Application Laid-Open No. Heisei 5 (1993)-109485
[Patent Reference 6] Japanese Patent Application Laid-Open No. 2004-002351
[Patent Reference 7] International Patent Application Laid-Open No. WO04/096945
[Patent Reference 8] Japanese Patent Application Laid-Open No. 2002-308837
[Patent Reference 9] Japanese Patent Application Laid-Open No. 2003-138251
[Patent Reference 10] Japanese Patent Application Laid-Open No. 2000-351966
[Patent Reference 11] International Patent Application Laid-Open No. WO04/095598

[Patent Reference 12] United States Patent No. 2004-209115
[Patent Reference 13] Japanese Patent Application Laid-Open No. 2004-103463
[Patent Reference 14] Japanese Patent Application Laid-Open No. 2005-183303
[Patent Reference 15] Japanese Patent Application Laid-Open No. 2005-317275
[Patent Reference 16] Japanese Patent Application Laid-Open No. 2004-200104
[Patent Reference 17] Japanese Patent Application Laid-Open No. 2005-310672
[Patent Reference 18] Japanese Patent Application Laid-Open No. 2005-306864
[Non-Patent Reference 1] D. F. O'Brien and M. A. Baldo et al. "Improved energy transferring electrophosphorescent devices" Applied Physics letters Vol. 74 No. 3, pp 442-444, Jan. 18, 1999
[Non-Patent Reference 2] M. A. Baldo et al. "Very high-efficiency green organic light-emitting devices based on electrophosphorescence" Applied Physics letters Vol. 75 No. 1, pp 4-6, Jul. 5, 1999

DISCLOSURE OF THE INVENTION

Problems to be Overcome by the Invention

The present invention has been made to overcome the above problems and has an object of providing an organic EL device providing excellent efficiency of light emission, forming no defects in pixels, exhibiting excellent heat resistance and having a long life and a material for organic EL devices which enables to obtain the device.

Means for Overcoming the Problems

As the result of intensive studies by the present inventors, it was found that an organic EL device providing excellent efficiency of light emission, forming no defects in pixels, exhibiting excellent heat resistance and having a long life could be obtained by using a compound represented by the following general formula (1) or (2) as the material for the organic EL device. The present invention has been completed based on the knowledge.

The present invention provides a material for organic EL devices which comprises a compound represented by the following general formula (1) or (2).

As the first aspect, the present invention provides a material for organic EL devices which comprises a compound represented by the following general formula (1):

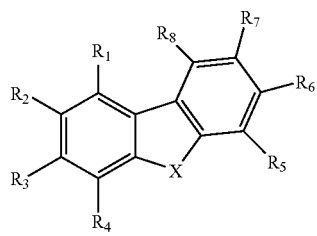

(1)

wherein $R_1$ to $R_8$ each independently represent hydrogen atom, a halogen atom, an alkyl group having 1 to 40 carbon atoms which may have substituents, a heterocyclic group having 3 to 20 carbon atoms which may have substituents, an alkoxyl group having 1 to 40 carbon atoms which may have substituents, a non-condensed aryl group having 6 to 40 carbon atoms which may have substituents, a condensed aryl group having 6 to 12 carbon atoms which may have substituents, an aryloxyl group having 6 to 20 carbon atoms which may have substituents, an aralkyl group having 7 to 20 carbon atoms which may have substituents, an alkenyl group having 2 to 40 carbon atoms which may have substituents, an alkylamino group having 1 to 40 carbon atoms which may have substituents, an aralkylamino group having 7 to 60 carbon atoms which may have substituents, an alkylsilyl group having 3 to 20 carbon atoms which may have substituents, an arylsilyl group having 8 to 40 carbon atoms which may have substituents, an aralkylsilyl group having 8 to 40 carbon atoms which may have substituents, an alkylgermanium group having 3 to 20 carbon atoms which may have substituents, an arylgermanium group having 8 to 40 carbon atoms which may have substituents, an aralkylgermanium group having 8 to 40 carbon atoms which may have substituents, a ketoaryl group having 7 to 40 carbon atoms which may have substituents, a halogenated alkyl group having 1 to 40 carbon atoms which may have substituents, cyano group or a structure represented by following general formula (a), and at least one of $R_1$ to $R_8$ has a structure represented by general formula (a):

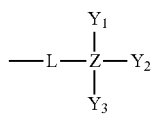

(a)

in general formula (a), L representing a single bond, an alkylene group having 1 to 10 carbon atoms which may have substituents, a non-condensed arylene group having 6 to 40 carbon atoms which may have substituents, a condensed arylene group having 6 to 12 carbon atoms which may have substituents or a divalent aromatic heterocyclic group having 3 to 40 carbon atoms which may have substituents, $Y_1$ to $Y_3$ each independently representing an alkyl group having 1 to 10 carbon atoms which may have substituents, an aryl group having 6 to 20 carbon atoms which may have substituents or an aromatic heterocyclic group having 6 to 30 carbon atoms which may have substituents, and Z representing silicon atom or germanium atom; and X represents sulfur atom, oxygen atom, a substituted silicon atom represented by $SiR_aR_b$ or a substituted germanium atom represented by $GeR_cR_d$, $R_a$, $R_b$, $R_c$, and $R_d$ each independently representing an alkyl group having 1 to 40 carbon atoms which may have substituents or an aryl group having 6 to 20 carbon atoms which may have substituents.

As the second aspect, the present invention provides a material for organic EL devices which comprises a compound represented by the following general formula (2):

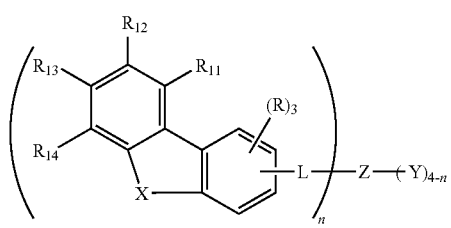

(2)

wherein $R_{11}$ to $R_{14}$ and R each independently represent hydrogen atom, a halogen atom, an alkyl group having 1 to 40 carbon atoms which may have substituents, a heterocyclic group having 3 to 20 carbon atoms which may have substituents, an alkoxyl group having 1 to 40 carbon atoms which may have substituents, a non-condensed aryl group having 6 to 40 carbon atoms which may have substituents, a condensed aryl group having 6 to 12 carbon atoms which may have substituents, an aryloxyl group having 6 to 20 carbon atoms which may have substituents, an aralkyl group having 7 to 20 carbon atoms which may have substituents, an alkenyl group having 2 to 40 carbon atoms which may have substituents, an alkylamino group having 1 to 40 carbon atoms which may have substituents, an aralkylamino group having 7 to 60 carbon atoms which may have substituents, an alkylsilyl group having 3 to 20 carbon atoms which may have substituents, an arylsilyl group having 8 to 40 carbon atoms which may have substituents, an aralkylsilyl group having 8 to 40 carbon atoms which may have substituents, an alkylgermanium group having 3 to 20 carbon atoms which may have substituents, an arylgermanium group having 8 to 40 carbon atoms which may have substituents, an aralkylgermanium group having 8 to 40 carbon atoms which may have substituents, a ketoaryl group having 7 to 40 carbon atoms which may have substituents, a halogenated alkyl group having 1 to 40 carbon atoms which may have substituents or cyano group;

X, L and Z are as defined in general formula (1), Y is as defined for $Y_1$ to $Y_3$ in general formula (1), and n represents an integer of 1 to 4.

The present invention also provides an organic electroluminescence device which comprises a cathode, an anode and an organic thin film layer which comprises at least one layer comprising at least a light emitting layer and is disposed between the cathode and the anode, wherein at least one layer in the organic thin film layer comprises the material for organic electroluminescence devices described above.

The Effect of the Invention

An organic EL device providing excellent efficiency of light emission, forming no defects in pixels, exhibiting excellent heat resistance and having a long life can be obtained when the material for organic EL devices comprising the compound represented by general formula (1) or (2) is used.

THE MOST PREFERRED EMBODIMENT TO CARRY OUT THE INVENTION

The present invention provides a material for organic EL devices comprising a compound represented by the following general formula (1) or (2).

The compound represented by general formula (1) will be described in the following.

In general formula (1), $R_1$ to $R_8$ each independently represent hydrogen atom, a halogen atom, an alkyl group having 1 to 40 carbon atoms which may have substituents, a heterocyclic group having 3 to 20 carbon atoms which may have substituents, an alkoxyl group having 1 to 40 carbon atoms which may have substituents, a non-condensed aryl group having 6 to 40 carbon atoms which may have substituents, a condensed aryl group having 6 to 12 carbon atoms which may have substituents, an aryloxyl group having 6 to 20 carbon atoms which may have substituents, an aralkyl group having 7 to 20 carbon atoms which may have substituents, an alkenyl group having 2 to 40 carbon atoms which may have substituents, an alkylamino group having 1 to 40 carbon atoms which may have substituents, an aralkylamino group having 7 to 60 carbon atoms which may have substituents, an alkylsilyl group having 3 to 20 carbon atoms which may have substituents, an arylsilyl group having 8 to 40 carbon atoms which may have substituents, an aralkylsilyl group having 8 to 40 carbon atoms which may have substituents, an alkylgermanium group having 3 to 20 carbon atoms which may have substituents, an arylgermanium group having 8 to 40 carbon atoms which may have substituents, an aralkylgermanium group having 8 to 40 carbon atoms which may have substituents, a ketoaryl group having 7 to 40 carbon atoms which may have substituents, a halogenated alkyl group having 1 to 40 carbon atoms which may have substituents, cyano group or a structure represented by following general formula (a), and at least one of $R_1$ to $R_8$ has a structure represented by general formula (a).

Examples of the halogen atom include fluorine, chlorine, bromine and iodine.

Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopentyl group, cyclohexyl group, cyclooctyl group, 3,5-tetramethylcyclohexyl group.

Among these alkyl groups, methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 1-pentylhexyl group, 1-butylpentyl group, 1-heptyloctyl group, cyclohexyl group, cyclooctyl group, 3,5-tetramethylcyclohexyl group are preferable.

Examples of the heterocyclic group include 1-pyrrolyl group, 2-pyrrolyl group, 3-pyrrolyl group, pyrazinyl group, 2-pyridinyl group, 1-imidazolyl group, 2-imidazolyl group, 1-pyrazolyl group, 1-indolidinyl group, 2-indolidinyl group, 3-indolidinyl group, 5-indolidinyl group, 6-indolidinyl group, 7-indolidinyl group, 8-indolidinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 9-carbazolyl group, β-carbolin-1-yl, β-carbolin-3-yl, β-carbolin-4-yl, β-carbolin-5-yl, β-carbolin-6-yl, β-carbolin-7-yl, β-carbolin-6-yl, β-carbolin-9-yl, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-silafluorenyl group, 2-silafluorenyl group, 3-silafluorenyl group, 4-silafluorenyl group, 1-germafluorenyl group, 2-germafluorenyl group, 3-germafluorenyl group and 4-germafluorenyl group.

Among these heterocyclic groups, 2-pyridinyl group, 1-indolidinyl group, 2-indolidinyl group, 3-indolidinyl group, 5-indolidinyl group, 6-indolidinyl group, 7-indolidinyl group, 8-indolidinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 1-carbazolyl group, 2-carbazolyl group, 3-carbazolyl group, 4-carbazolyl group, 9-carbazolyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-silafluorenyl group, 2-silafluorenyl group, 3-silafluorenyl group, 4-silafluorenyl group, 1-germafluorenyl group, 2-germafluorenyl group, 3-germafluorenyl group and 4-germafluorenyl group are preferable.

The alkoxyl group is a group represented by —OY. Examples of the group represented by Y include the groups described above as the examples of the alkyl group, and preferable examples of the group represented by Y include the groups described as the preferable examples of the alkyl group.

Examples of the non-condensed aryl group include phenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl-p-terphenyl-4-yl group, o-cumenyl group, m-cumenyl group, p-cumenyl group, 2,3-xylyl group, 3,4-xylyl group, 2,5-xylyl group, mesityl group and m-quater-phenyl group.

Among these groups, phenyl group, 2-biphenylyl group, 3-biphenylyl group, 4-biphenylyl group, m-terphenyl-4-yl group, m-terphenyl-3-yl group, m-terphenyl-2-yl group, p-tolyl group, 3,4-xylyl group and m-quarterphenyl-2-yl group are preferable.

Examples of the condensed aryl group include 1-naphthyl group and 2-naphthyl group.

The aryloxyl group is a group represented by —OAr. Examples of the group represented by Ar include the groups described above as the examples of the non-condensed aryl group. Preferable examples of the group represented by Ar include the groups described as the preferable examples of the non-condensed aryl group.

Examples of the aralkyl group include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β- naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

Among these aralkyl groups, benzyl group, p-cyanobenzyl group, m-cyanobenzyl group, o-cyanobenzyl group, 1-phenylethyl group, 2-phenylethyl group, 1-phenylisopropyl group and 2-phenylisopropyl groups are preferable.

Examples of the alkenyl group include vinyl group, allyl group, 1-butenyl group, 2-butenyl group, 3-butenyl group, 1,3-butadienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl-1-butenyl group and 3-phenyl-1-butenyl group. Among these groups, styryl group, 2,2-diphenylvinyl group and 1,2-diphenylvinyl group are preferable.

The alkylamino group and the aralkylamino group having 7 to 60 carbon atoms which may have substituents are represented by —NQ$_1$Q$_2$. Examples of the groups represented by Q$_1$ and Q$_2$, each independently, include the groups described above as the examples of the alkyl group, the aryl group and the aralkyl group. Preferable examples of the groups represented by Q$_1$ and Q$_2$ include the groups described above as the preferable examples of the alkyl group, the aryl group and the aralkyl group.

Examples of the alkylsilyl group include trimethylsilyl group, triethylsilyl group, t-butyldimethylsilyl group, vinyldimethylsilyl group and propyldimethylsilyl group.

Examples of the arylsilyl group include triphenylsilyl group, tribiphenylsilyl group, diterphenylphenylsilyl group, phenyldimethylsilyl group and t-butyldiphenylsilyl group.

Examples of the aralkylsilyl group include tribenzylsilyl group, benzyldimethylsilyl group and t-butylbenzylsilyl group.

Examples of the alkylgermanium group include trimethylgermanium group, triethylgermanium group, t-butyldimethylgermanium group, vinyldimethylgermanium group and propyldimethylgermanium group.

Examples of the arylgermanium group include triphenylgermanium group, tribiphenylgermanium group, diterphenylphenylgermanium group, phenyldimethylgermanium group and t-butyldiphenylgermanium group.

Examples of the aralkylgermanium group include tribenzylgermanium group, benzyldimethylgermanium group and t-butyldibenzylgermanium group.

The ketoaryl group is a group represented by —COAr$_2$. Examples of the group represented by Ar$_2$ include the groups described above as the examples of the aryl group. Preferable examples of the group represented by Ar$_2$ include the groups described above as the preferable examples of the aryl group.

Examples of the halogenated alkyl group include the alkyl groups described above wherein at least one hydrogen atom of the alkyl group is substituted with at least one halogen atom. Preferable examples of the halogenated alkyl group include the alkyl groups described above as the preferable examples wherein at least one hydrogen atom of the alkyl group is substituted with at least one halogen atom.

In general formula (1), X represents sulfur atom, oxygen atom, a substituted silicon atom represented by SiR$_a$R$_b$ or a substituted germanium atom represented by GeR$_c$R$_d$. R$_a$, R$_b$, R$_c$, and R$_d$ each independently represent an alkyl group having 1 to 40 carbon atoms which may have substituents or an aryl group having 6 to 20 carbon atoms which may have substituents.

Examples of the alkyl group represented by R$_a$, R$_b$, R$_c$, and R$_d$ include the groups described above as the examples of the alkyl group represented by R$_1$ to R$_8$. Preferable examples include methyl group, ethyl group, propyl group and butyl group.

Examples of the aryl group having 6 to 20 carbon atoms represented by R$_a$, R$_b$, R$_c$ and R$_d$ include the groups described above as the examples of the non-condensed aryl group represented by R$_1$ to R$_8$. Preferable examples include phenyl group, p-tolyl group, and 4-biphenyl group.

General formula (a) shows the following structure:

(a)

In general formula (a), L represents a single bond, an alkylene group having 1 to 10 carbon atoms which may have substituents, a non-condensed arylene group having 6 to 40 carbon atoms which may have substituents, a condensed arylene group having 6 to 12 carbon atoms which may have substituents or a divalent aromatic heterocyclic group having 3 to 40 carbon atoms which may have substituents.

Examples of the alkylene group represented by L include divalent groups derived from the groups described as the examples of the alkyl group represented by R$_1$ to R$_8$. Among these groups, methylene group, ethylene group, propylene group, butylene group, divalent cyclohexane groups, divalent adamantane groups and divalent norbornene groups are preferable.

Examples of the non-condensed arylene group represented by L include divalent groups derived from the groups described as the examples of the non-condensed aryl group represented by R$_1$ to R$_8$. Among these groups, divalent groups such as phenylene group, para-biphenylene group, meta-biphenylene group, ortho-biphenylene group, ortho-terphenylene group, meta-terphenylene group and para-terphenylene group are preferable.

Examples of the condensed arylene group include divalent residue groups derived from naphthalene and the like.

Examples of the aromatic heterocyclic group represented by L include divalent residue groups having skeleton structures derived from mother skeleton structures of pyridine, pyrazine, quinoline, pyrimidine, triazine, thiophene, silole, benzofuran, benzothiophene, dibenzofuran, dibenzothiophene, carbazole, quinoline, furan, pyrrol, imidazole, pyrazole, isothiazole, isoxazole, isoquinoline, quinazoline, quinolidine, quinoxaline, cinnoline, benzimidazole, imidazopyridine, naphthylidine, 1,2-benzoisoxazole, benzoxazole, benzothiazole, oxazolopyridine, isothiazolopyridine and benzothienyl. Among these groups, divalent residue groups having skeleton structures derived from mother skeleton structures of pyridine, pyrazine, quinoline, pyrimidine, thiophene, silole, dibenzofuran, dibenzothiophene, imidazopyridine and benzimidazole are preferable.

In general formula (a), $Y_1$ to $Y_3$ each independently represent an alkyl group having 1 to 10 carbon atoms which may have substituents, an aryl group having 6 to 20 carbon atoms which may have substituents or an aromatic heterocyclic group having 6 to 30 carbon atoms which may have substituents.

Examples of the alkyl group represented by $Y_1$ to $Y_3$ include the groups described above as the examples of the alkyl group represented by $R_1$ to $R_8$.

Examples of the aryl group represented by $Y_1$ to $Y_3$ include the groups described above as the examples of the non-condensed aryl group and the condensed aryl group represented by $R_1$ to $R_8$.

Examples of the aromatic heterocyclic group represented by $Y_1$ to $Y_3$ include furyl group, thienyl group, pyrrolyl group, imidazolyl group, pyrazolyl group, isothiazolyl group, isoxazolyl group, pyridyl group, pyrimidinyl group, quinolyl group, isoquinolyl group, quinazolinyl group, quinolidinyl group, quinoxalinyl group, cinnolinyl group, benzimidazolyl group, imidazopyridyl group, benzofuranyl group, naphthylidinyl group, 1,2-benzoisoxazolyl group, benzoxazolyl group, benzothiazolyl group, oxazolopyridyl group, isothiazolopyridyl group and benzothienyl group.

In general formula (a), Z represents silicon atom or germanium atom.

The compound represented by general formula (2), will be described in the following.

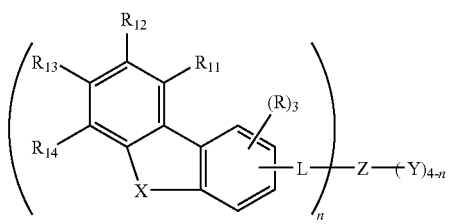

(2)

In general formula (2), $R_{11}$ to $R_{14}$ and R each independently represent hydrogen atom, a halogen atom, an alkyl group having 1 to 40 carbon atoms which may have substituents, a heterocyclic group having 3 to 20 carbon atoms which may have substituents, an alkoxyl group having 1 to 40 carbon atoms which may have substituents, a non-condensed aryl group having 6 to 40 carbon atoms which may have substituents, a condensed aryl group having 6 to 12 carbon atoms which may have substituents, an aryloxyl group having 6 to 20 carbon atoms which may have substituents, an aralkyl group having 7 to 20 carbon atoms which may have substituents, an alkenyl group having 2 to 40 carbon atoms which may have substituents, an alkylamino group having 1 to 40 carbon atoms which may have substituents, an aralkylamino group having 7 to 60 carbon atoms which may have substituents, an alkylsilyl group having 3 to 20 carbon atoms which may have substituents, an arylsilyl group having 8 to 40 carbon atoms which may have substituents, an aralkylsilyl group having 8 to 40 carbon atoms which may have substituents, an alkylgermanium group having 3 to 20 carbon atoms which may have substituents, an arylgermanium group having 8 to 40 carbon atoms which may have substituents, an aralkylgermanium group having 8 to 40 carbon atoms which may have substituents, a ketoaryl group having 7 to 40 carbon atoms which may have substituents, a halogenated alkyl group having 1 to 40 carbon atoms which may have substituents or cyano group.

Examples of the groups described above include the groups described above as the examples of the corresponding groups represented by $R_1$ to $R_8$ in general formula (1).

In general formula (2), X, L and Z are as defined for X, L and Z, respectively, in general formula (1), and Y is as defined for $Y_1$ to $Y_3$ in general formula (1). Examples and preferable examples of the atoms and the groups include the atoms and the groups described as the examples and the preferable examples, respectively, of the corresponding atoms and groups in general formula (1).

In general formula (2), n represents an integer of 1 to 4. It is preferable that n represents 2 or 3 since the molecular weight has a suitable value, and both of the excellent property for sublimation and the excellent heat stability are sufficiently exhibited.

It is preferable that the compound represented by general formula (2) is a compound represented by the following general formula (3) or (4) since the compound can be easily prepared.

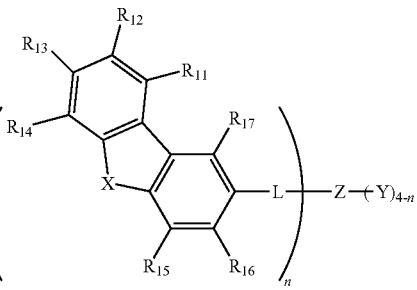

(3)

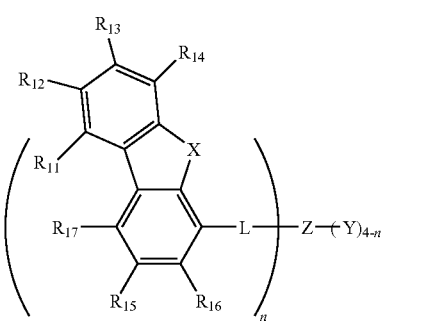

(4)

In general formulae (3) and (4), $R_{11}$ to $R_{17}$ are as defined for $R_{11}$ to $R_{14}$ and R in general formula (2). Examples and preferable examples of the atoms and the groups include the atoms and the groups described as the examples and the preferable examples, respectively, of the corresponding atoms and groups in general formula (2). L, X, Z, Y and n are as defined for L, X, Z, Y and n, respectively, in general formula (2).

Examples of the substituent to the groups in general formulae (1) to (4) include alkyl groups (methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromo-isopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbornyl group and 2-norbornyl group), alkoxyl groups having 1 to 6 carbon atoms (ethoxyl group, methoxyl group, i-propoxyl group, n-propoxyl group, s-butoxyl group, t-butoxyl group, pentoxyl group, hexyloxyl group, cyclopentoxyl group and cyclohexyloxyl group), aryl groups having 5 to 40 ring carbon atoms, amino groups substituted with aryl groups having 5 to 40 ring carbon atoms, ester groups having aryl groups having 5 to 40 ring carbon atoms, cyano group, nitro group and halogen atoms.

Specific examples of the material for organic EL devices of the present invention which comprises the compound represented by one of general formulae (1) to (4) are shown in the following. However, the material for organic EL devices of the present invention is not limited to the compounds shown in the following.

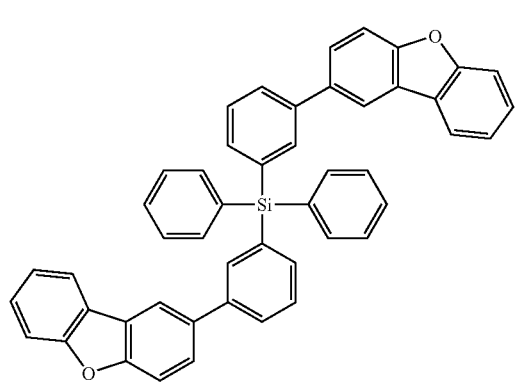

A-1

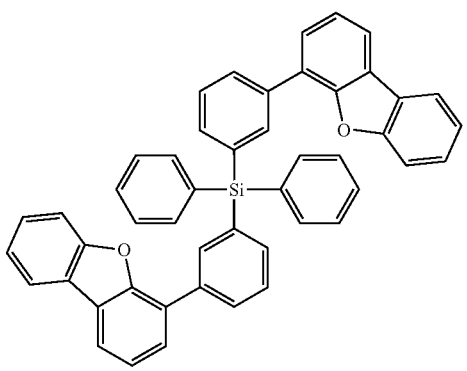

A-2

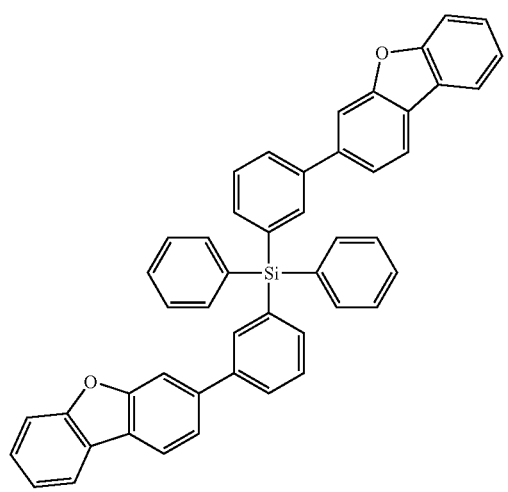

A-3

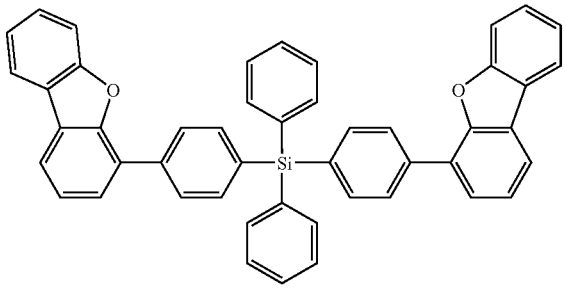

A-4

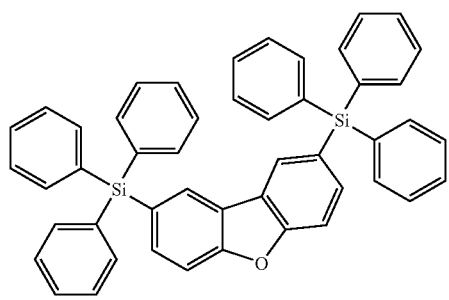

A-5

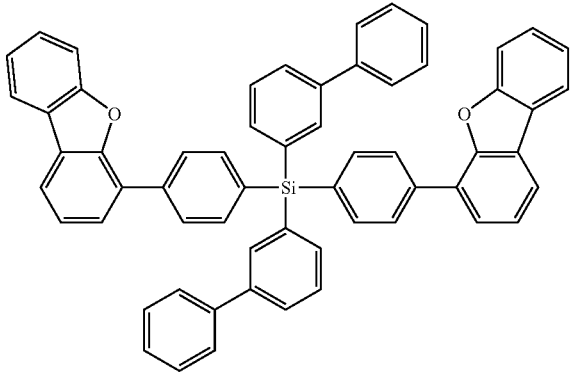

A-6

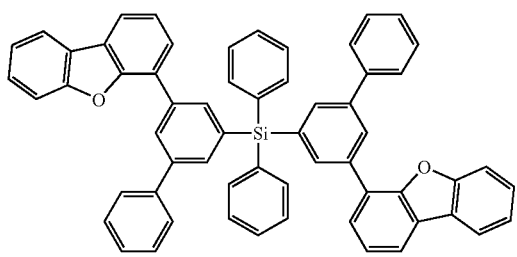
A-7
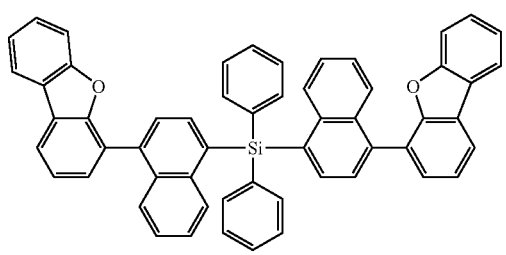
A-8
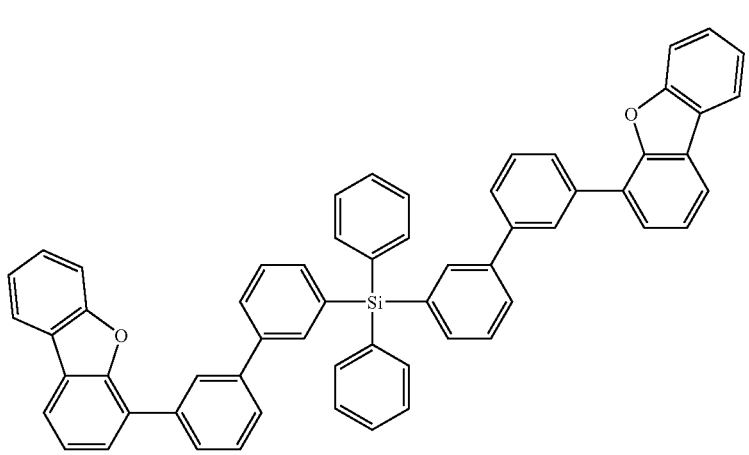
A-9
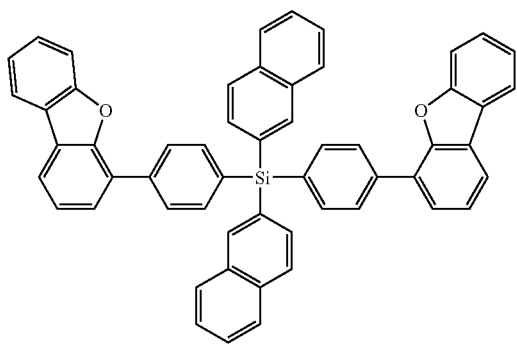
A-10
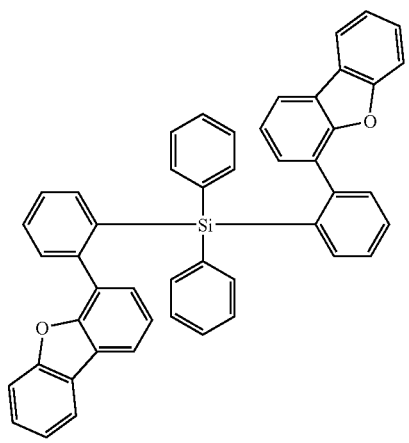
A-11

-continued
A-12
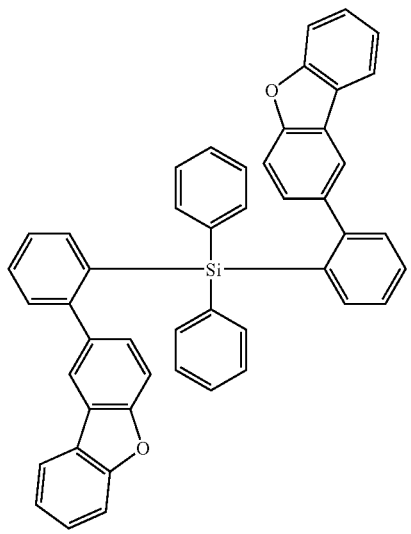
A-13
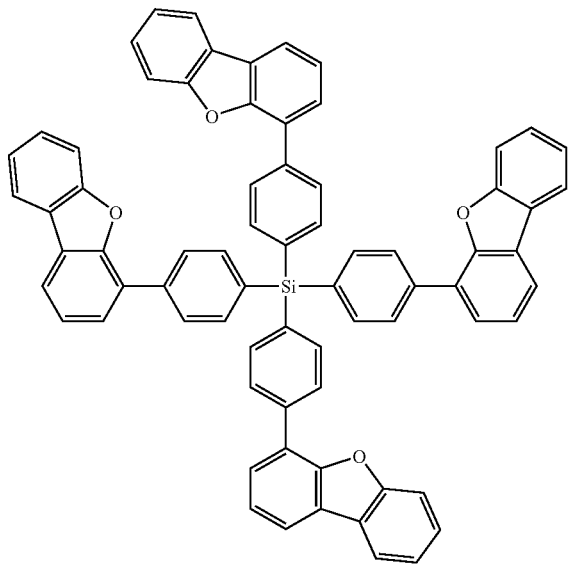
A-14
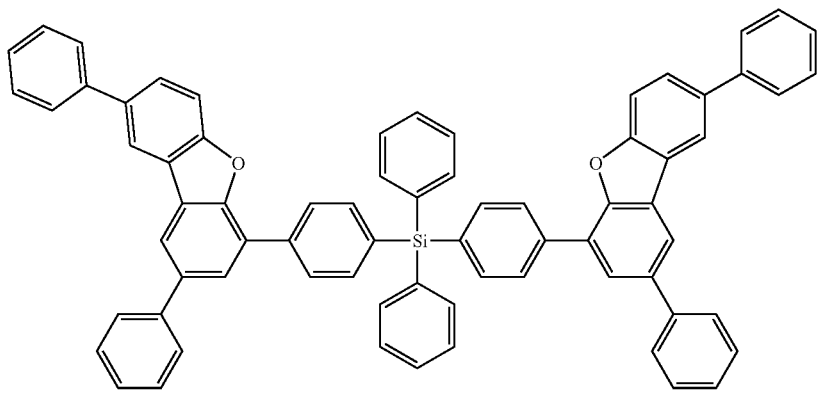
B-1
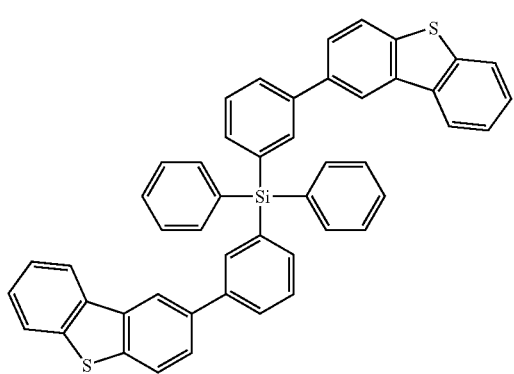
B-2
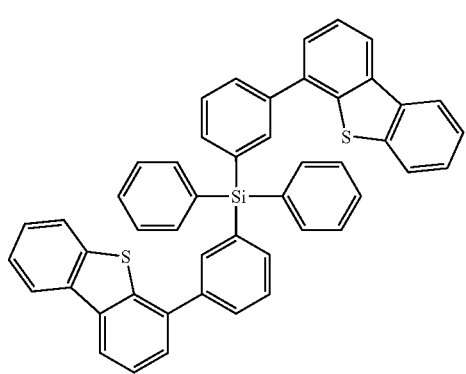

-continued
B-3
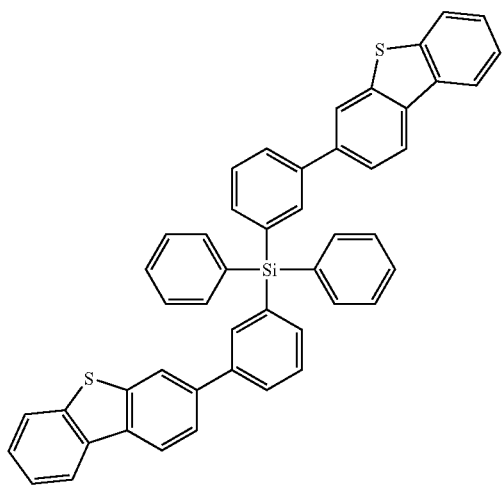
B-4
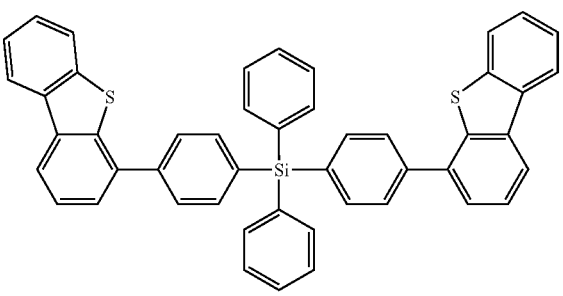
B-5
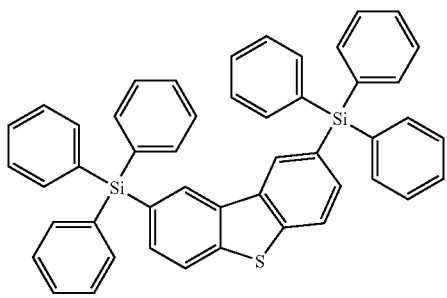
B-6
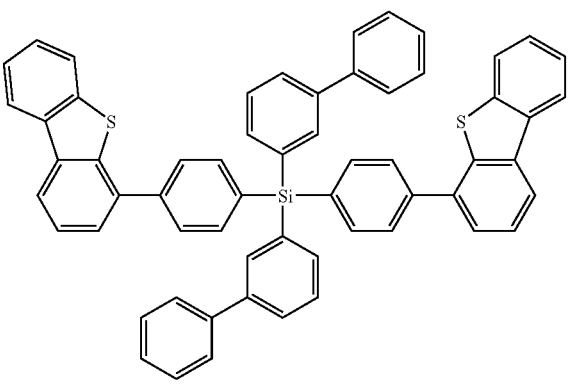
B-7
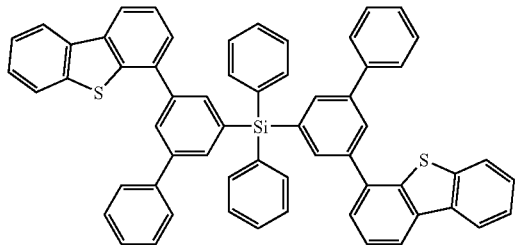
B-8
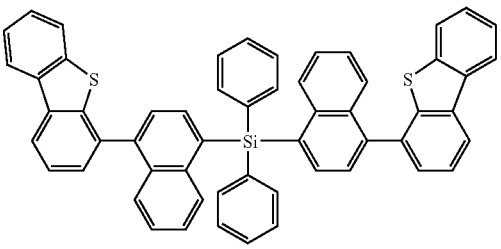
B-9
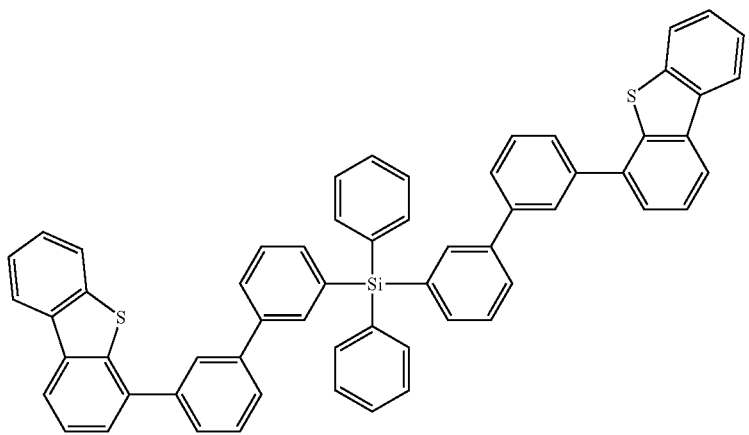

-continued
B-10
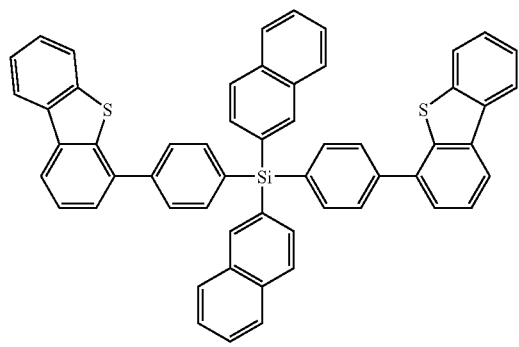
B-11
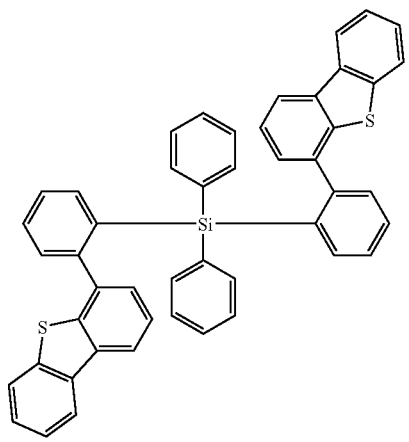
B-12
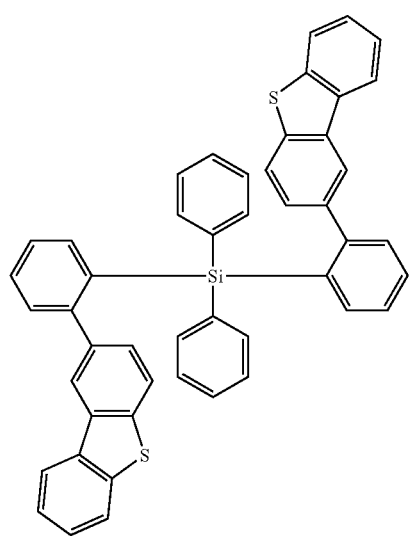
B-13
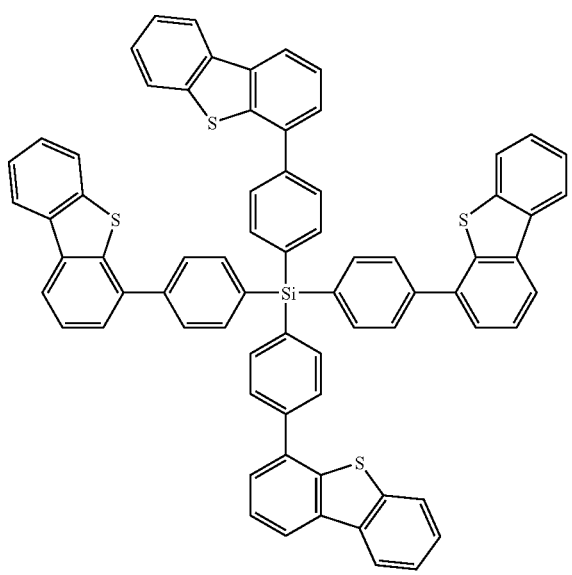
B-14
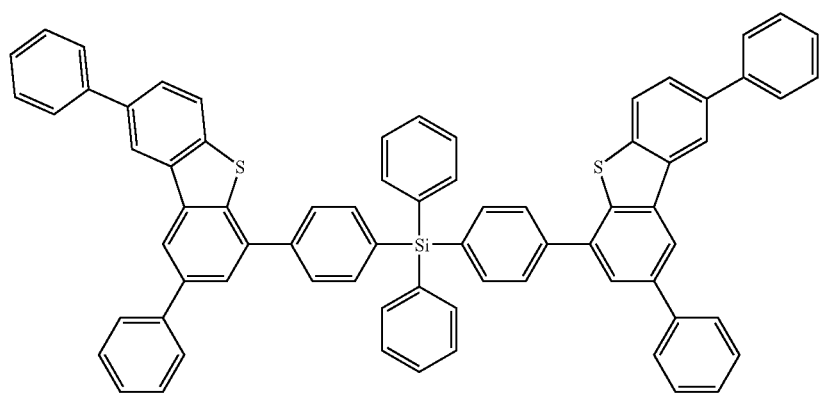

-continued
C-1
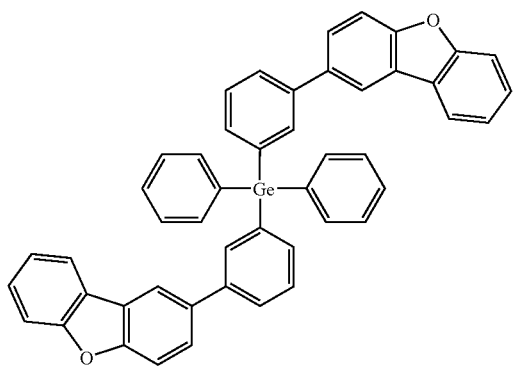
C-2
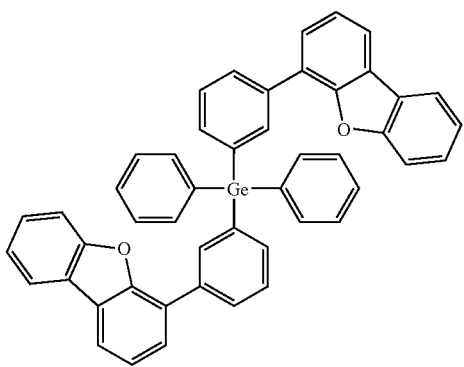
C-3
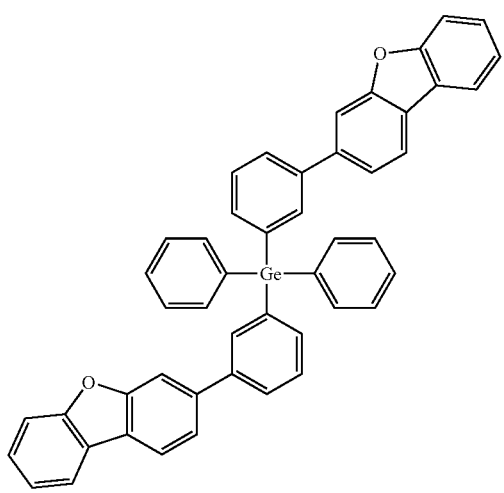
C-4
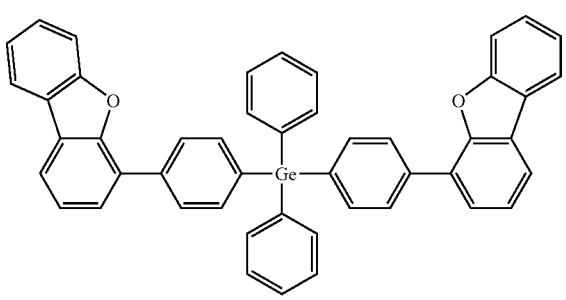
C-5
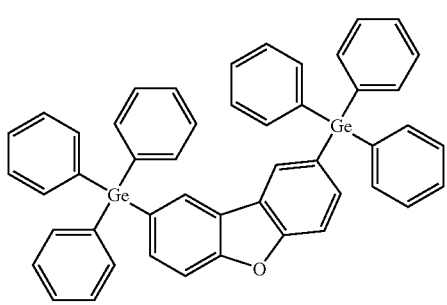
C-6
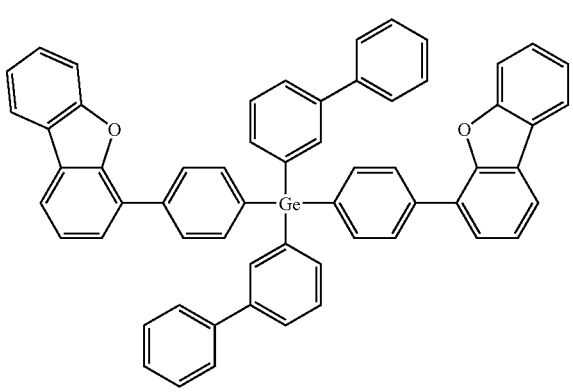
C-7
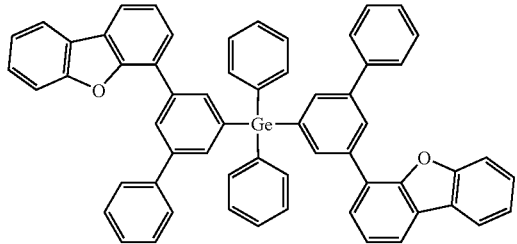
C-8
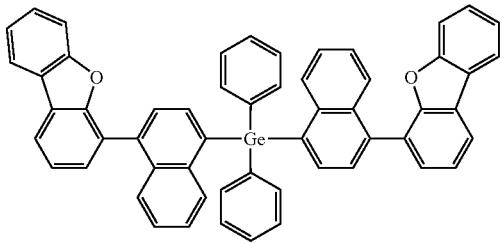

-continued
C-9
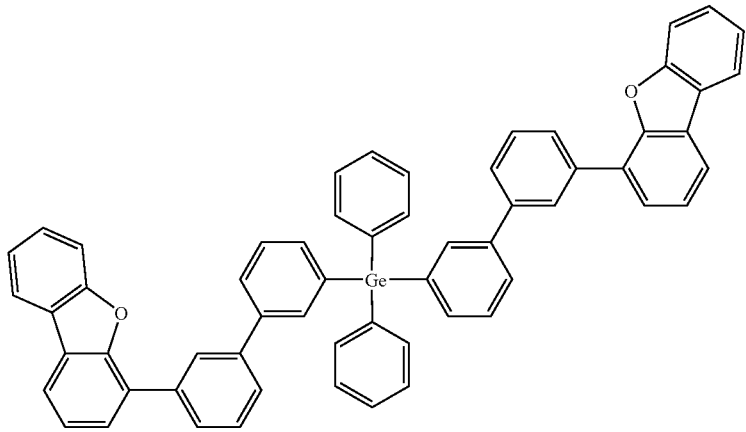
C-10
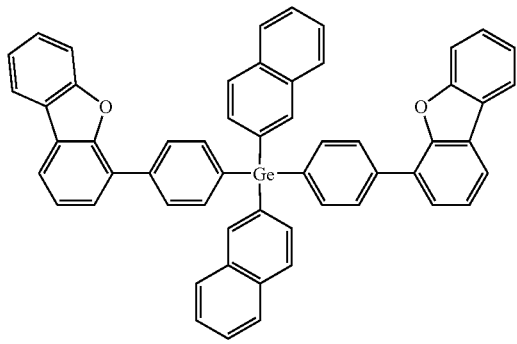
C-11
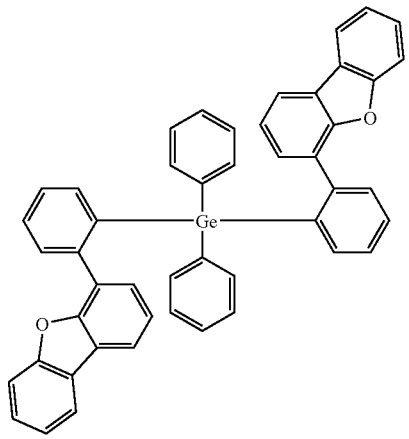
C-12
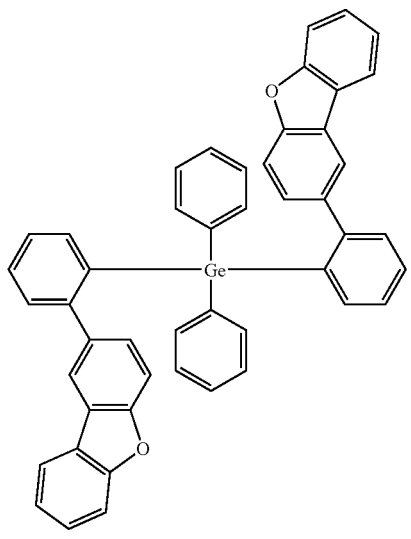
C-13
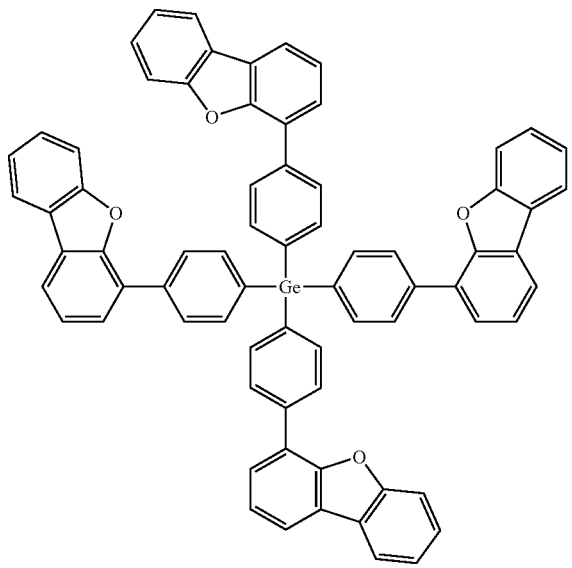

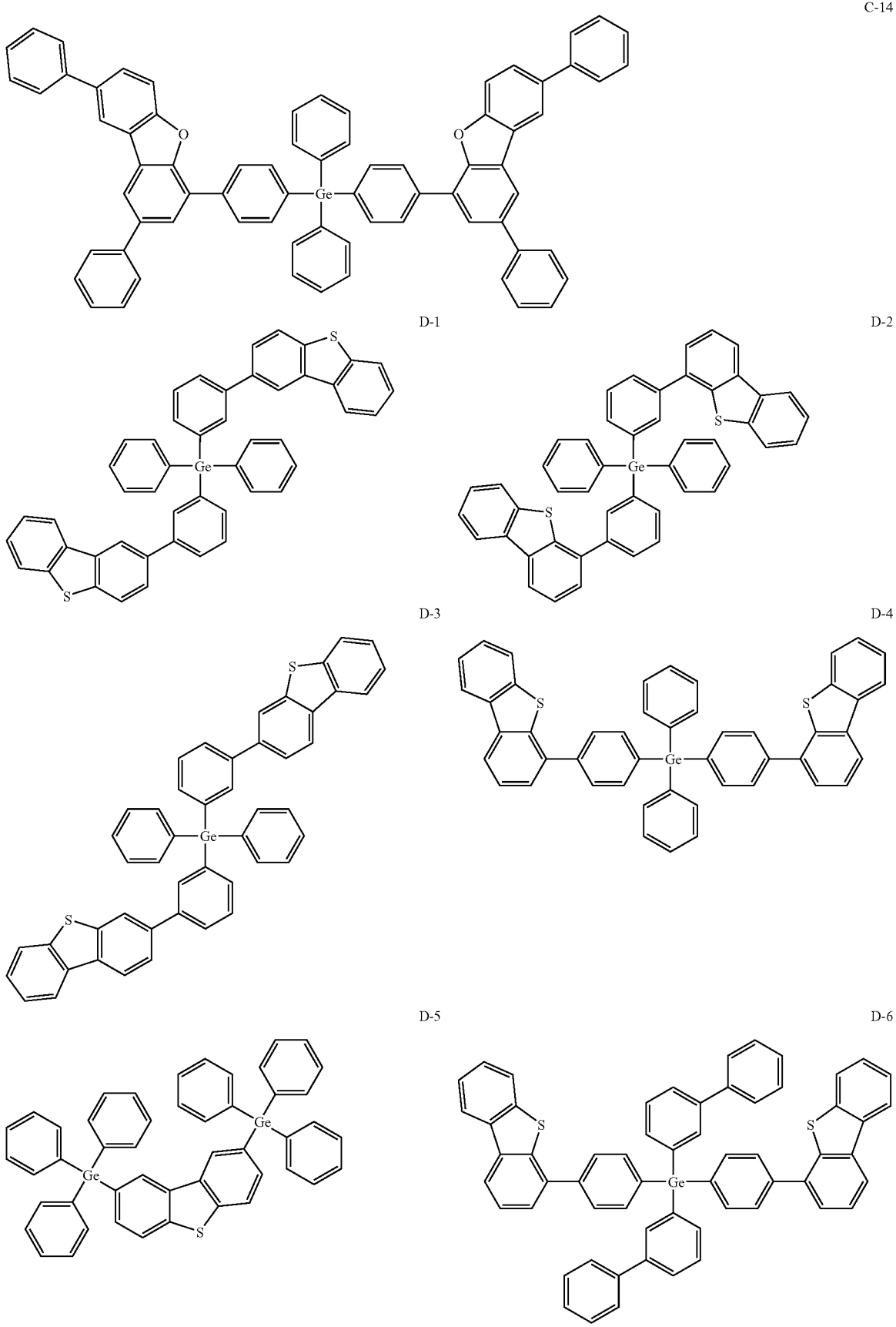

-continued
D-7
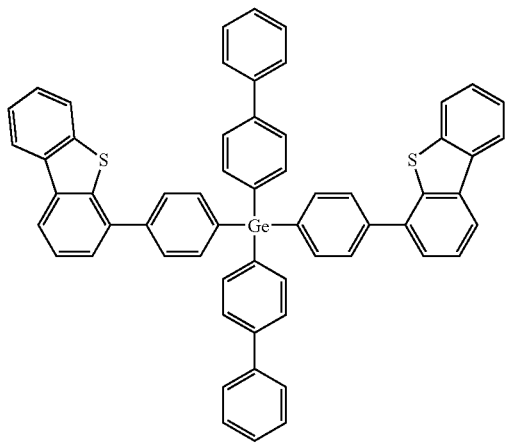
D-8
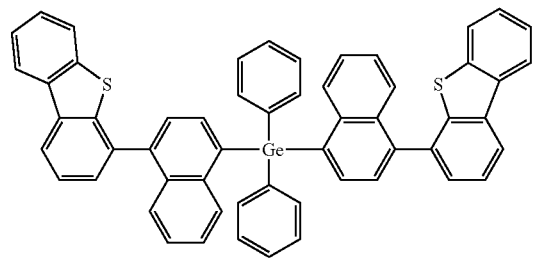
D-9
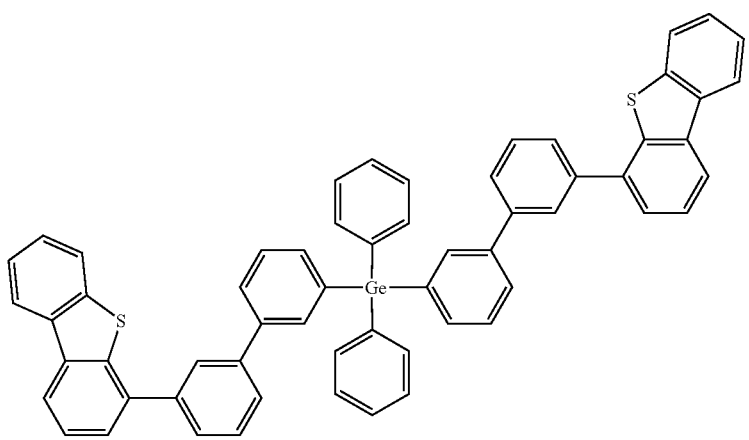
D-10
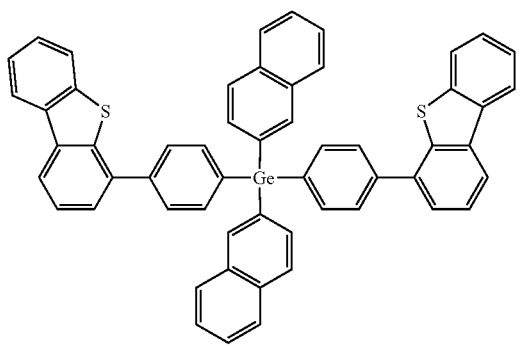
D-11
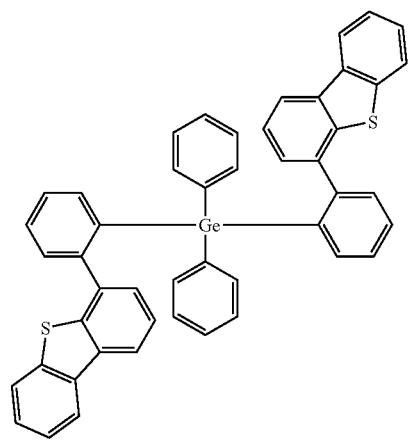

-continued
D-12
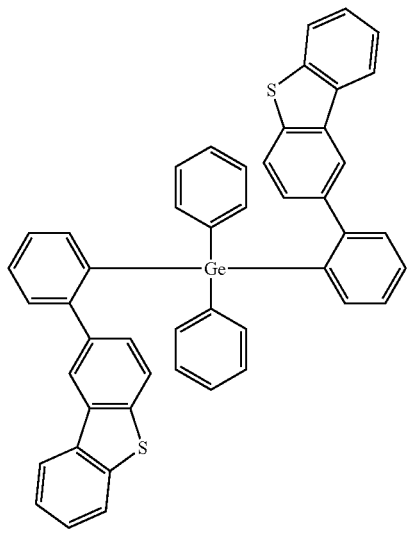
D-13
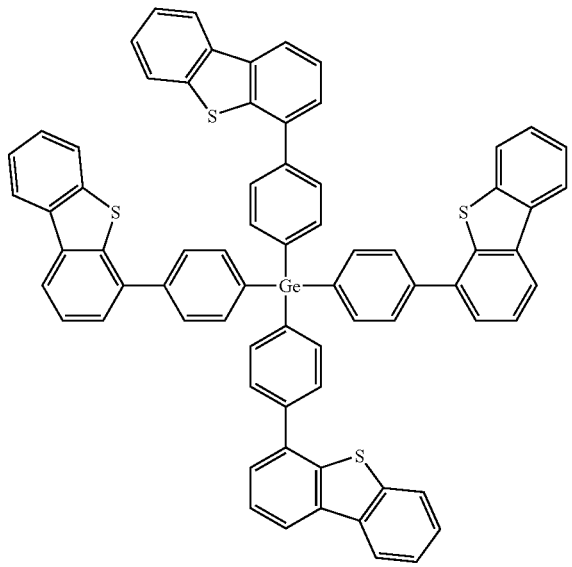
D-14
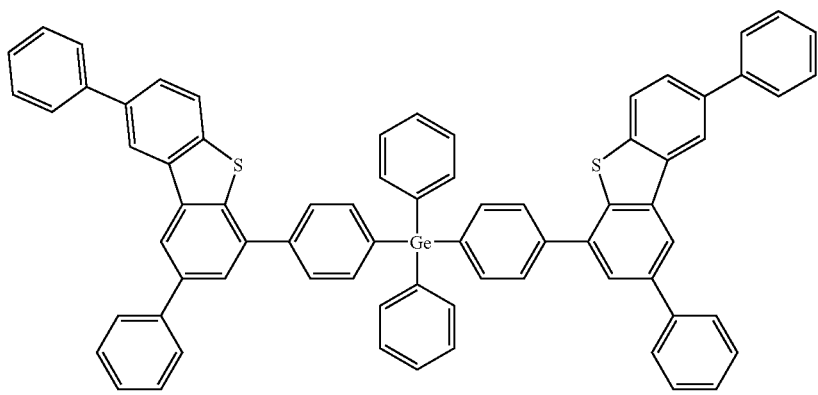
E-1
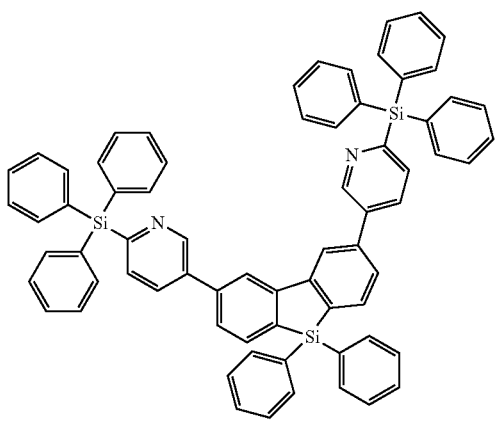
E-2
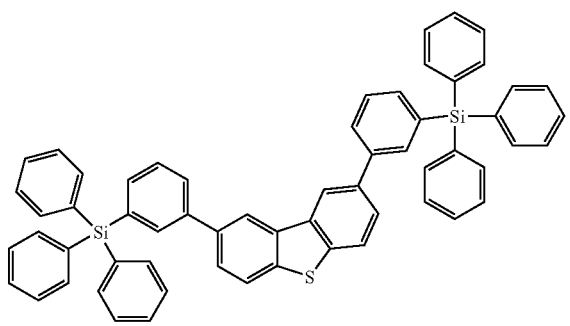

-continued
E-3
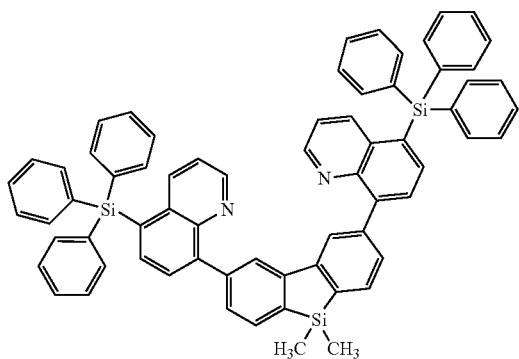
E-4
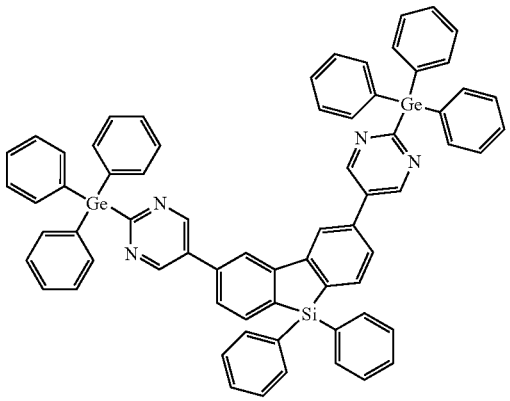
E-5
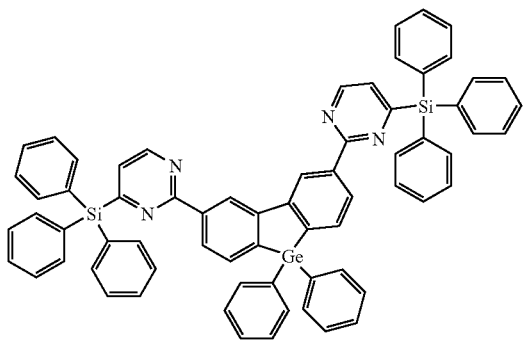
E-6
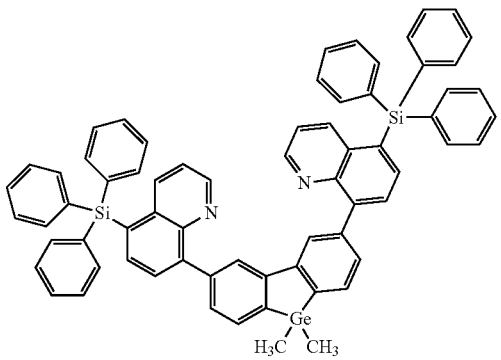
E-7
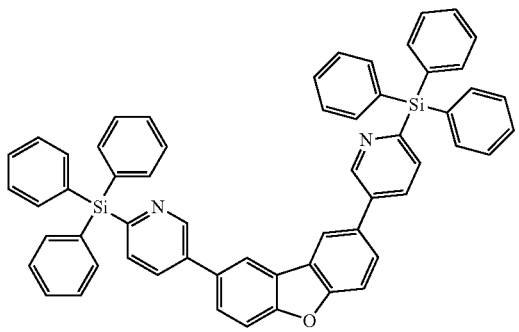
E-8
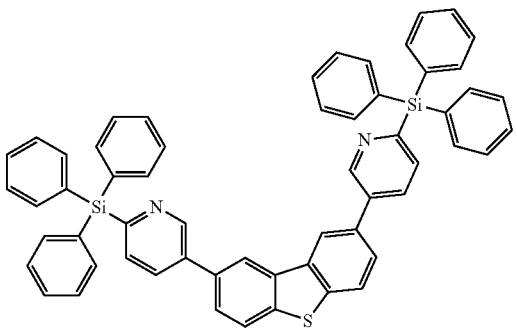
E-9
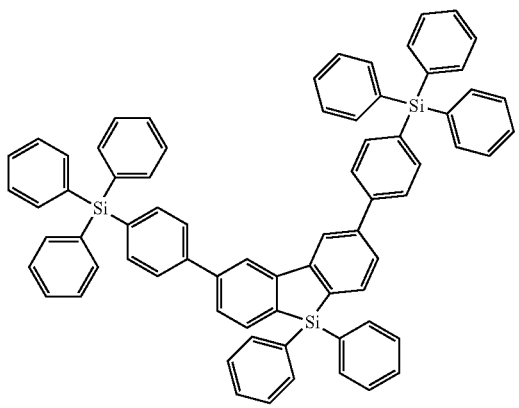
E-10
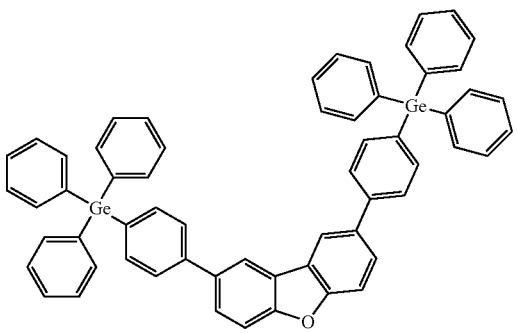

It is preferable that the material for organic EL devices of the present invention is a host material comprised in the light emitting layer of the organic EL device.

The organic EL device of the present invention will be described in the following.

The organic EL device of the present invention comprises a cathode, an anode and an organic thin film layer which comprises at least one layer comprising at least a light emitting layer and is disposed between the cathode and the anode, wherein at least one layer in the organic thin film layer comprises the material for organic EL devices described above.

Examples of the construction of the organic EL device of the multiple layer type include constructions obtained by laminating a plurality of layers such as (an anode/a hole transporting layer (a hole injecting layer)/a light emitting layer/a cathode), (an anode/a light emitting layer/an electron transporting layer (an electron injecting layer)/a cathode), (an anode/a hole transporting layer (a hole injecting layer)/a light emitting layer/an electron transporting layer (an electron injecting layer)/a cathode) and (an anode/a hole transporting layer (a hole injecting layer)/a light emitting layer/a hole barrier layer/an electron transporting layer (an electron injecting layer)/a cathode).

In the organic EL device of the present invention, it is preferable that the light emitting layer comprises the material for organic EL devices of the present invention as the host material. It is preferable that the light emitting layer comprises the host material and a phosphorescent light emitting material, and the host material is the material for organic EL devices of the present invention.

As the phosphorescent light emitting material, compounds having a metal selected from iridium (Ir), osmium (Os) and platinum (Pt) are preferable, and metal complex compounds such as iridium complex compounds, osmium complex compounds and platinum complex compounds are more preferable, iridium complex compounds and platinum complex compounds are still more preferable, and iridium complex compounds formed into ortho metals are most preferable since the quantum yield of phosphorescence is great and the external quantum efficiency of the light emitting device can be further increased. Examples of the preferable form of the metal complex compound formed into an orthometal include iridium complexes shown in the following:

(K-1)

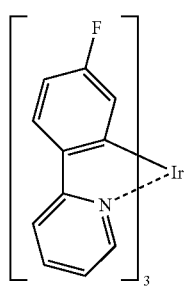

(K-2)

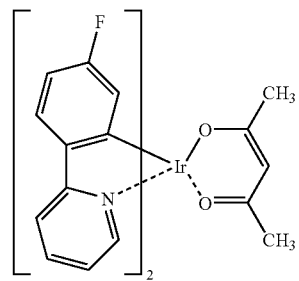

(K-3)

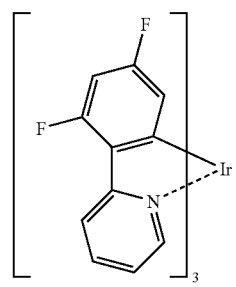

(K-4)

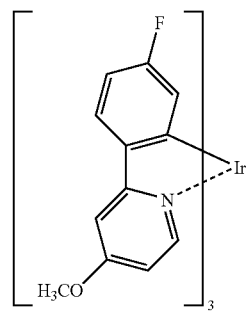

(K-5)

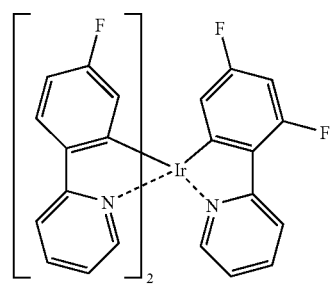

(K-6)

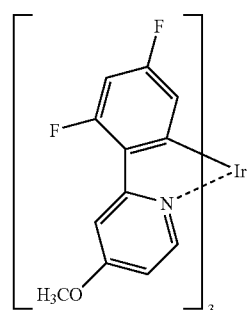

(K-7)
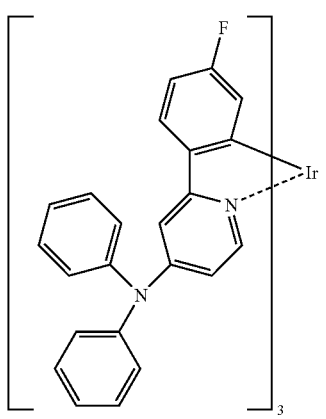
(K-8)
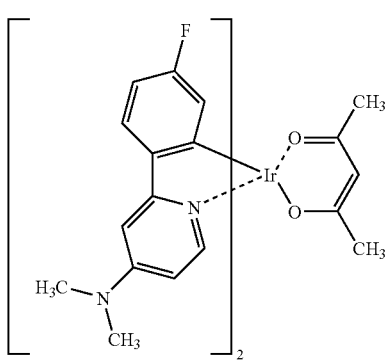
(K-9)
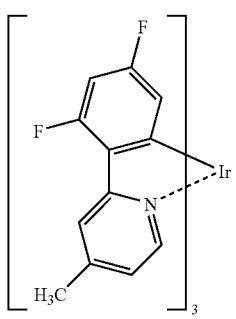
(K-10)
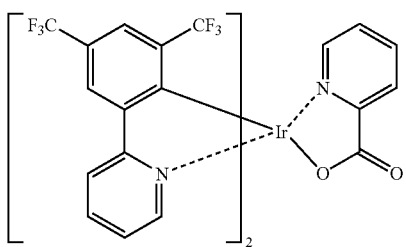
(K-11)
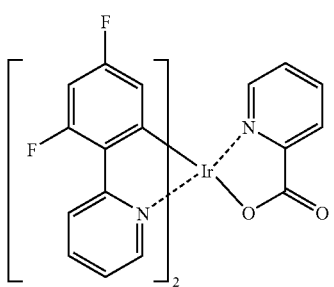
(K-12)
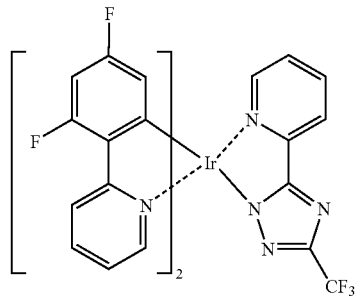
(K-13)
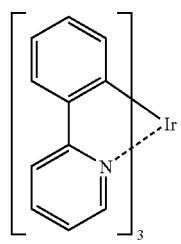
(K-14)
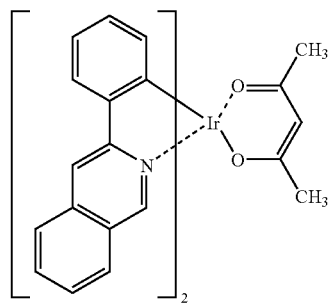
(K-15)
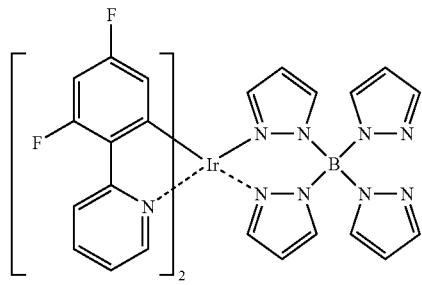
(K-16)
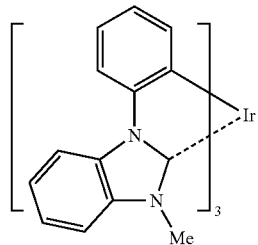

-continued

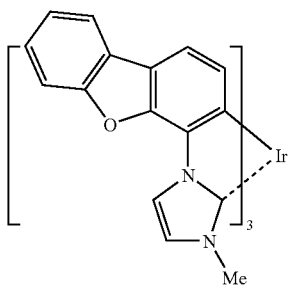
(K-17)

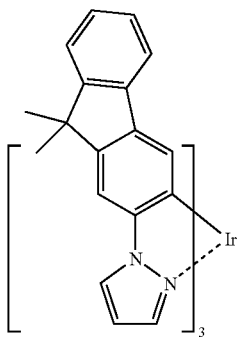
(K-18)

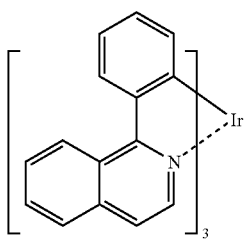
(K-19)

In the organic EL device of the present invention, it is preferable that the light emitting layer comprises a host material and a phosphorescent light emitting material, and the phosphorescent light emitting material is a light emitting material having a metal-carbene carbon bond.

It is preferable that the light emitting layer comprises a metal complex compound emitting bluish light which exhibits a maximum luminance at a wavelength of 500 nm or smaller. Examples of the metal complex compound emitting bluish light include K-1, K-2, K-3, K-10, K-11, K-12, K-15, K-16 and K-17 which are shown above.

It is preferable that the organic EL device of the present invention comprises a hole transporting layer (a hole injecting layer), and the hole transporting layer (the hole injecting layer) comprises the material for organic electroluminescence devices of the present invention. It is preferable that the organic EL device of the present invention comprises at least one of an electron transporting layer (an electron injecting layer) and a hole barrier layer, and at least one of the electron transporting layer (the electron injecting layer) and the hole barrier layer comprises the material for organic electroluminescence devices of the present invention.

The hole injecting layer is a layer disposed for efficiently injecting holes from the anode into the organic EL device. The driving voltage can be decreased and the change in the carrier balance by the driving can be suppressed by smoothly injecting holes from the anode into the layer. As the material used for the hole injecting layer, in general, a compound having an ionization potential energy close to the work function of the metal of the anode is used. Example of the material used for the hole injecting layer include arylamine compounds, complex compounds of various metals such as copper and iridium and hexaazatriphenylene derivatives.

The hole transporting layer is a layer having the function of transporting holes injected from the anode and delivering the holes to the light emitting layer. Holes and electrons are recombined efficiently in the light emitting layer and the efficiency of light emission can be increased by disposing the hole transporting layer. To exhibit this effect, it is required for the material used for the hole transporting layer that the function of efficiently transporting the holes to the light emitting layer be exhibited. In general, as the material used for the hole transporting layer, an arylamine-based material is used. In general, a material providing a mobility of holes of $10^{-5}$ cm$^2$/Vs or greater under the condition such that the intensity of the electric field raised to ½ power is in the range of 300 to 800 $(V/cm)^{1/2}$ is preferable. It is preferable that the hole injecting layer and the hole transporting layer comprise the material for organic EL devices of the present invention.

The hole barrier layer is a layer disposed between the light emitting layer and the cathode so that electrons and holes are efficiently recombined in the light emitting layer. For the hole barrier layer, a substance having a first oxidation potential greater than that of the material for the light emitting layer. Injection of holes into the electron transporting layer can be prevented by disposing the hole barrier layer. Examples of the material used for the hole barrier layer include materials for the hole barrier layer described in Japanese Patent No. 2673261.

The electron transporting layer is a layer having the function of transporting electrons injected from the cathode and delivering the electrons to the light emitting layer. Holes and electrons are recombined efficiently in the light emitting layer and the efficiency of light emission can be increased by disposing the electron transporting layer. It is necessary for efficiently obtain the light emission of EL that electrons are efficiently delivered to the light emitting layer. As the material used for the electron transporting layer, in general, aromatic compounds having nitrogen atom, hetero compounds having a hetero atom other than nitrogen atom such as silol compounds, complex compounds of metals such as aluminum and gallium and condensed aromatic hydrocarbons are used. In general, these compounds have a mobility of electrons of $10^{-6}$ cm$^2$/Vs or greater under the condition such that the intensity of the electric field raised to ½ power is in the range of 300 to 800 $(V/cm)^{1/2}$. As the electron transporting material, compounds which will be described below are preferable. It is also preferable that the electron transporting layer and the hole barrier layer comprise the material for organic EL devices of the present invention.

The electron injecting layer is a layer disposed for efficiently injecting electrons from the cathode into the organic EL device. Electrons can be smoothly injected from the cathode by disposing the electron injecting layer. Therefore, the driving voltage can be decreased, and the change in the carrier balance due to the driving can be suppressed. As the material constituting the electron injecting layer, materials which will be described below are preferable.

In the organic EL device of the present invention, it is preferable that a reducing dopant is added at the interfacial region between the cathode and the organic thin film layer.

As the reducing dopant, at least one substance selected from the group consisting of alkali metals, complex compounds of alkali metals, alkali metal compounds, alkaline earth metals, complex compounds of alkaline earth metals, alkaline earth metal compounds, rare earth metals, complex compounds of rare earth metals and rare earth metal compounds is used.

Examples of the alkali metal include Na (the work function: 2.36 eV), K (the work function: 2.28 eV), Rb (the work function: 2.16 eV) and Cs (the work function: 1.95 eV). Alkali metals having a work function of 2.9 eV or smaller are preferable. Among these alkali metals, K, Rb and Cs are preferable, Rb and Cs are more preferable, and Cs is most preferable.

Examples of the alkaline earth metal include Ca (the work function: 2.9 eV), Sr (the work function: 2.0 to 2.5 eV) and Ba (the work function: 2.52 eV). Alkaline earth metals having a work function of 2.9 eV or smaller are preferable.

Examples of the rare earth metal include Sc, Y, Ce, Th and Yb. Rare earth metals having a work function of 2.9 eV or smaller are preferable.

The preferable metals among the above metals exhibit great reducing ability, and the increase in the luminance of light emitted from the organic EL device and the increase in the life of the organic EL device can be achieved by addition of a relatively small amount into the electron injecting region.

Examples of the alkali metal compound include oxides of alkali metals such as $Li_2O$, $Cs_2O$ and $K_2O$ and halides of alkali metals such as LiF, NaF, CsF and KF. Oxides and fluorides of alkali metals such as LiF, $Li_2O$ and NaF are preferable.

Examples of the alkaline earth metal compound include BaO, SrO, CaO and mixtures of these oxides such as $Ba_xSr_{1-x}O$ (0<x<1) and $Ba_xCa_{1-x}O$ (0<x<1). BaO, SrO and CaO are preferable.

Examples of the rare earth metal compound include $YbF_3$, $ScF_3$, $ScO_3$, $Y_2O_3$, $Ce_2O_3$, $GdF_3$ and $TbF_3$. $YbF_3$, $ScF_3$ and $TbF_3$ are preferable.

The complex compounds of alkali metals, the complex compounds of alkaline earth metals and the complex compounds of rare earth metals are not particularly limited as long as the complex compounds comprise at least one of alkali metal ions, alkaline earth metal ions and rare earth metal ions, respectively. As the ligand, quinolinol, benzoquinolinol, acridinol, phenanthridinol, hydroxyphenyloxazole, hydroxyphenylthiazole, hydroxydiaryloxadiazoles, hydroxydiarylthiadiazoles, hydroxyphenylpyridine, hydroxyphenylbenzimidazole, hydroxybenzotriazole, hydroxyfurborane, bipyridiyl, phenanthroline, phthalocyanine, porphyrin, cyclopentadiene, β-diketones, azomethines and derivatives of these compounds are preferable. However, the ligand is not limited to the above compounds.

As for the form of the added reducing dopant, it is preferable that the reducing dopant is formed in the form of a layer or islands. As the process for forming the reducing dopant, it is preferable that, while the reducing dopant is vapor deposited in accordance with the vapor deposition process using the resistance heating, the organic substance as the light emitting material or the electron injecting material forming the interfacial region is vapor deposited simultaneously so that the reducing dopant is dispersed in the organic substance. The concentration of the dispersion is 100:1 to 1:100 and preferably 5:1 to 1:5 as the ratio of the amounts by mole of the organic substance to the reducing dopant.

When the reducing dopant is formed in the form of a layer, after a layer of the light emitting material or the electron injecting material is formed as the organic layer at the interface, the reducing dopant alone is vapor deposited in accordance with the vapor deposition process using the resistance heating so that a layer preferably having a thickness of 0.1 to 15 nm is formed.

When the reducing dopant is formed in the form of islands, after the light emitting material or the electron injecting material as the organic layer at the interface is formed in the form of islands, the reducing dopant alone is vapor deposited in accordance with the vapor deposition process using the resistance heating so that islands preferably having a thickness of 0.05 to 1 nm are formed.

It is preferable that relative amounts of the main component and the reducing dopant in the organic EL device of the present invention is 5:1 to 1:5 and more preferably 2:1 to 1:2 as the ratio of the amounts by mole of the main component to the reducing dopant.

It is preferable that the organic EL device comprises the electron injecting layer disposed between the light emitting layer and the cathode, and the electron injecting layer comprises a cyclic derivative having nitrogen atom as a main component thereof since the amount of the skeleton structure enhancing adhesion with the cathode is increased.

As the electron transporting material used for the electron injecting layer, aromatic heterocyclic compounds having at least one hetero atom in the molecule are preferable, and cyclic derivatives having nitrogen atom are more preferable.

As the cyclic derivative having nitrogen atom, for example, derivatives represented by the following general formula (A) are preferable:

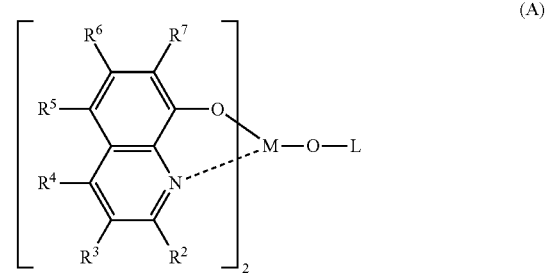

(A)

$R^2$ to $R^7$ each independently represent hydrogen atom, a halogen atom, oxy group, amino group or a hydrocarbon group having 1 to 40 carbon atoms, and the groups may have substituents.

Examples of the halogen atom include atoms described above as the examples of the halogen atom. Examples of the amino group having substituents include groups described above as the examples of the alkylamino group, the arylamino group and the aralkylamino group.

Examples of the hydrocarbon group having 1 to 40 carbon atoms include alkyl groups, alkenyl groups, cycloalkyl groups, alkoxyl groups, aryl groups, heterocyclic groups, aralkyl groups, aryloxyl groups and alkoxycarbonyl groups, which may be substituted or unsubstituted. Examples of the alkyl groups, the alkenyl group, the cycloalkyl group, the alkoxyl group, the aryl group, the heterocyclic group, the aralkyl group and the aryloxyl group include the groups described above as the examples of the corresponding groups. The alkoxycarbonyl group is a group represented by —COOY'. Examples of the group represented by Y' include the groups described above as the examples of the alkyl group.

M represents aluminum (Al), gallium (Ga) or indium (In), and it is preferable that M represents In.

L in general formula (A) represents a group represented by the following general formula (A') or (A"):

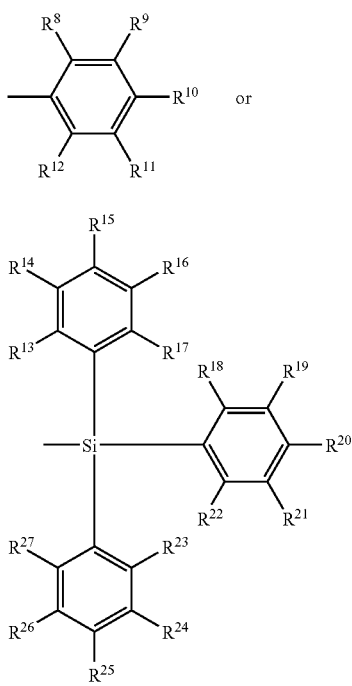

(A')

(A")

In the above general formulae, $R^8$ to $R^{12}$ each independently represent hydrogen atom or a substituted or unsubstituted hydrocarbon group having 1 to 40 carbon atoms, and groups adjacent to each other may form a cyclic structure. $R^{13}$ to $R^{27}$ each independently represent hydrogen atom or a substituted or unsubstituted hydrocarbon group having 1 to 40 carbon atoms, and groups adjacent to each other may form a cyclic structure.

Examples of the hydrocarbon groups having 1 to 40 carbon atoms which are represented by $R^8$ to $R^{12}$ and $R^{13}$ to $R^{27}$ in general formulae (A') and (A") include the groups described above as the examples of the groups represented by $R^2$ to $R^7$.

When groups adjacent to each other form a cyclic structure among the groups represented by $R^8$ to $R^{12}$ and $R^{13}$ to $R^{27}$, examples of the formed divalent group include tetramethylene group, pentamethylene group, hexamethylene group, diphenylmethane-2,2'-diyl group, diphenylethane-3,3'-diyl group and diphenylpropane-4,4'-diyl group.

Specific examples of the chelate complex compound of a metal having nitrogen atom, which is represented by general formula (A), are shown in the following. However, the cyclic derivative having nitrogen atom is not limited to the compounds shown as the examples.

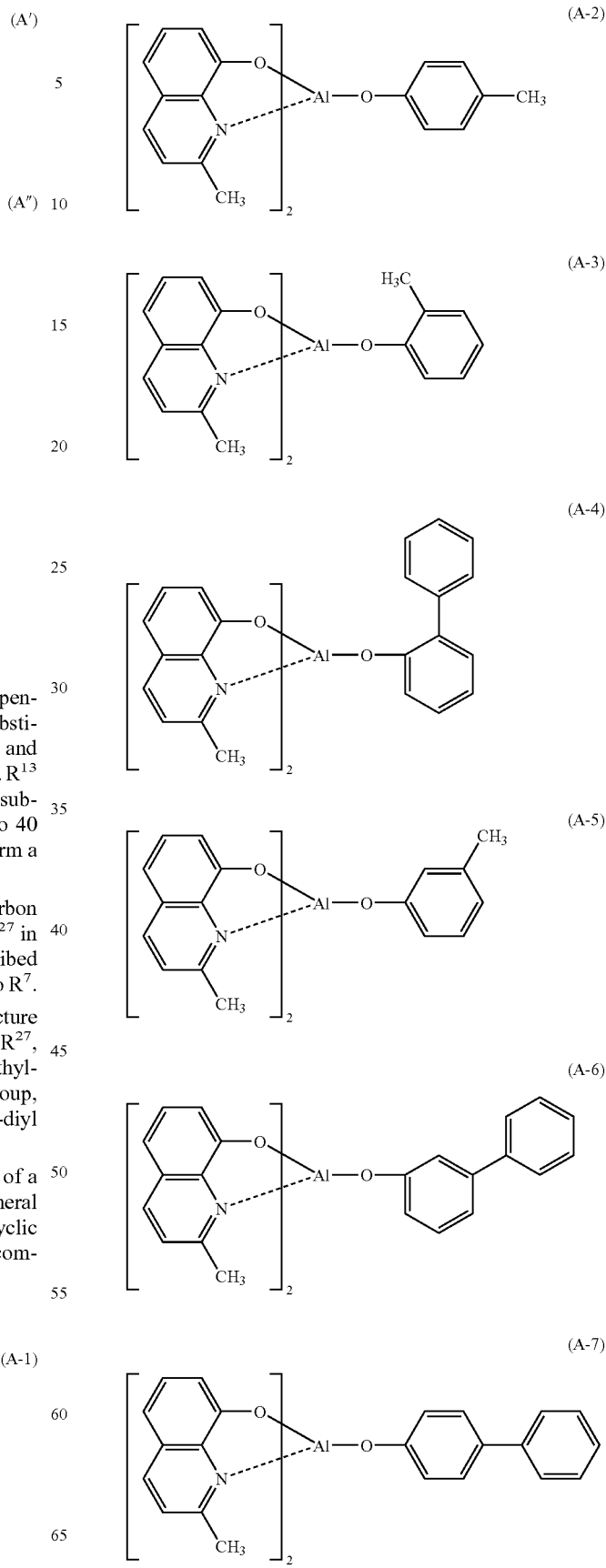

(A-8)
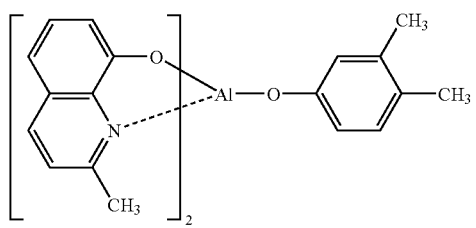
(A-9)
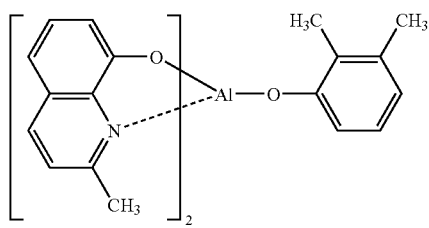
(A-10)
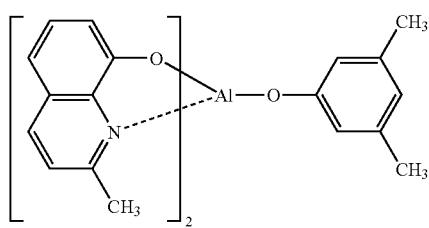
(A-11)
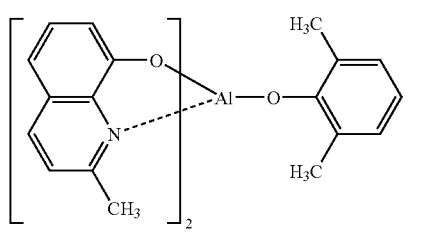
(A-12)
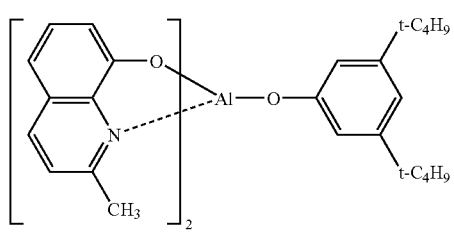
(A-13)
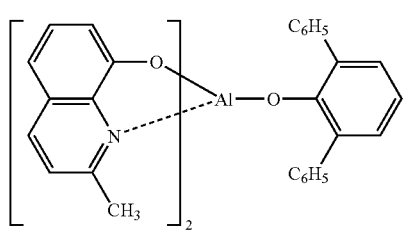
(A-14)
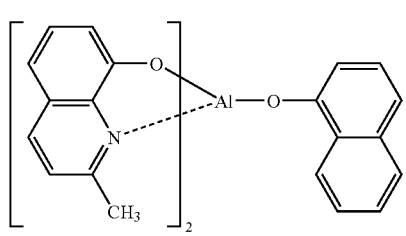
(A-15)
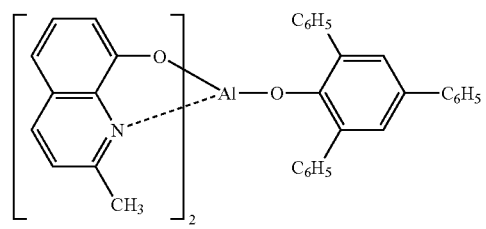
(A-16)
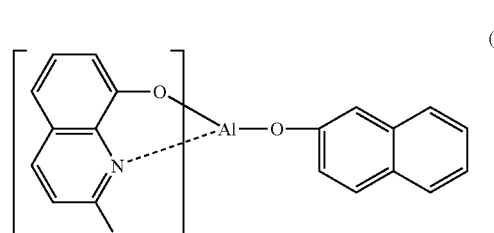
(A-17)
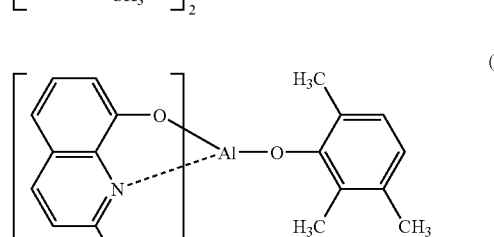
(A-18)
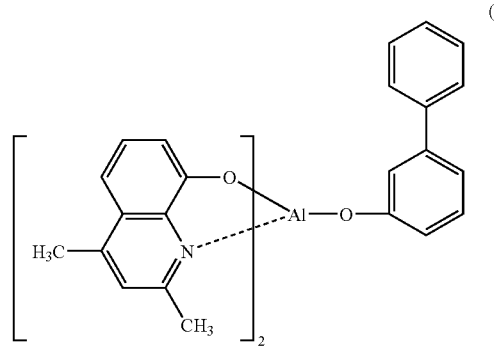
(A-19)
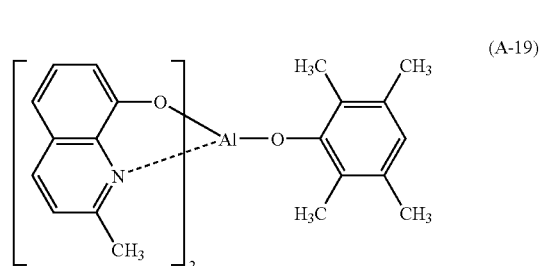
(A-20)
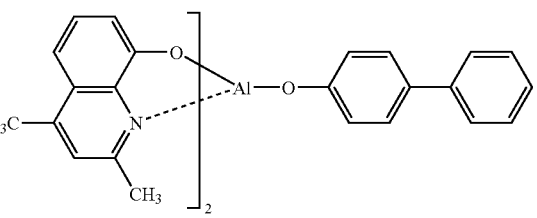

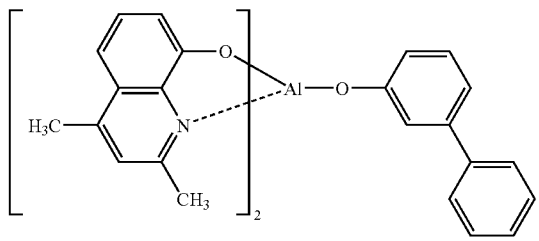
(A-21)
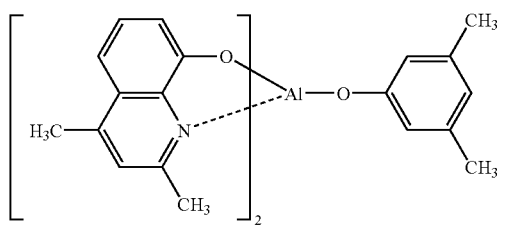
(A-22)
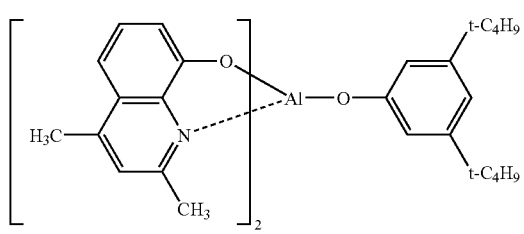
(A-23)
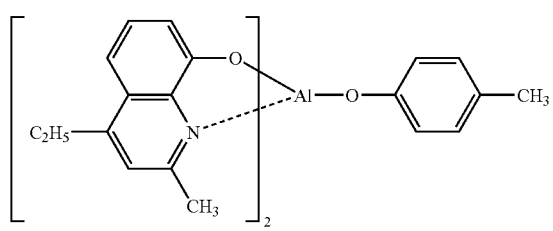
(A-24)
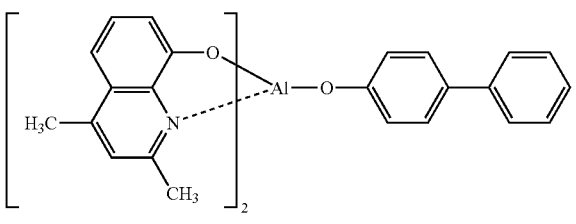
(A-25)
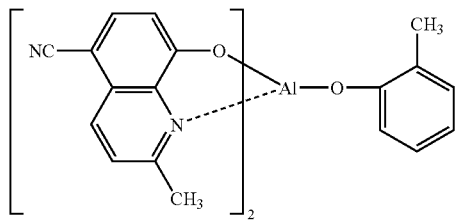
(A-26)
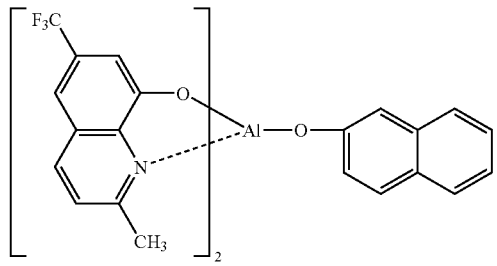
(A-27)
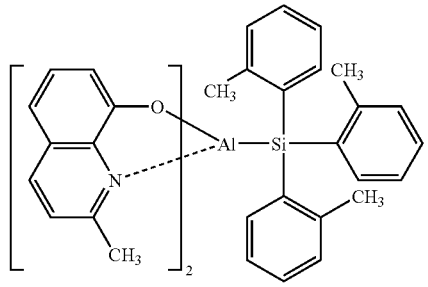
(A-28)
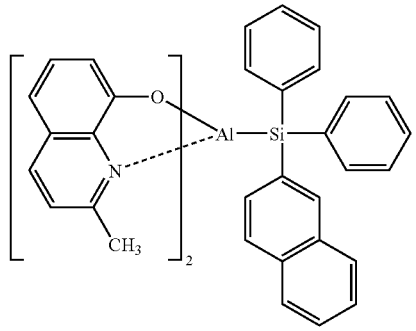
(A-29)
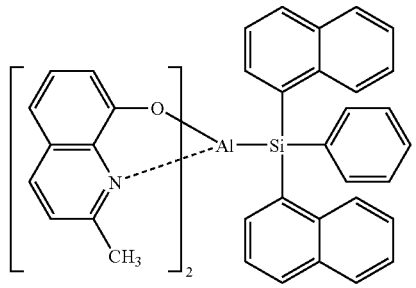
(A-30)
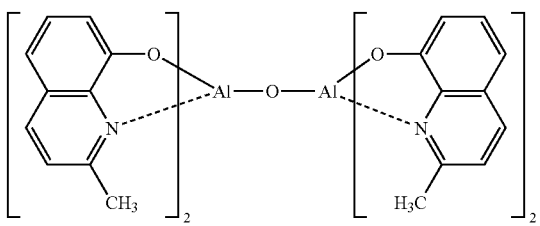
(A-31)

(A-32)
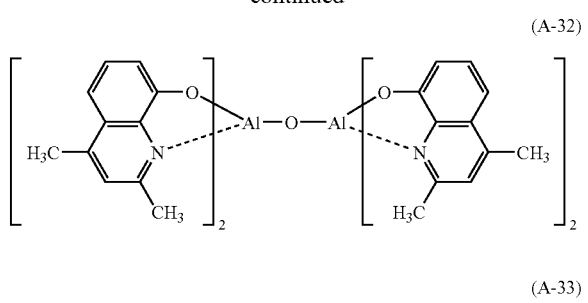

(A-33)
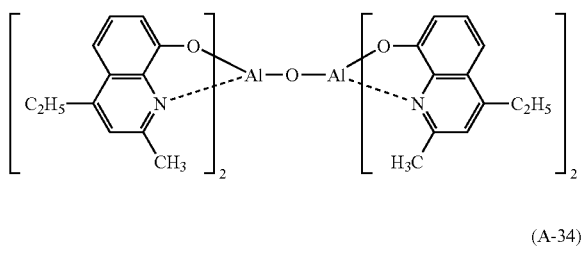

(A-34)
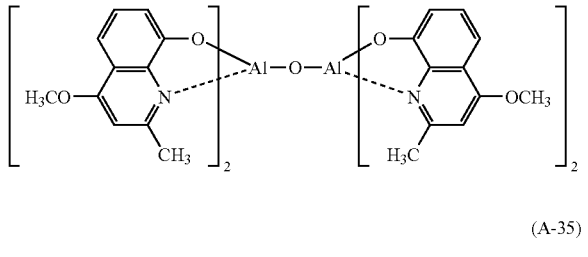

(A-35)
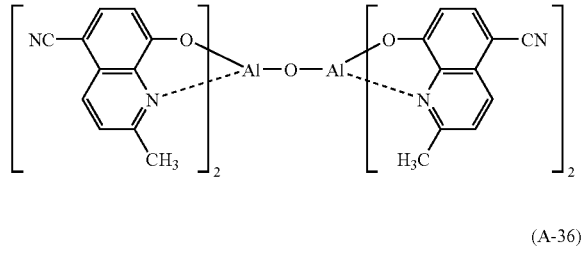

(A-36)
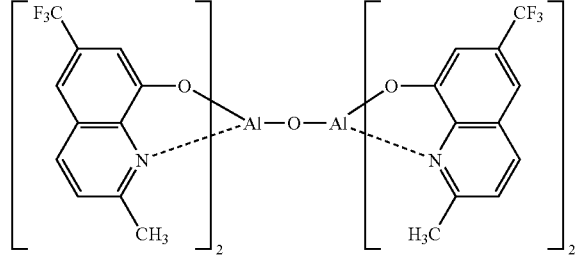

As the cyclic derivative having nitrogen atom described above, five-membered cyclic derivatives having nitrogen atom are also preferable. Examples of the five-membered ring having nitrogen atom include imidazole ring, triazole ring, tetrazole ring, oxadiazole ring, thiadiazole ring, oxatriazole ring and thiatriazole ring. Examples of the five-membered cyclic derivative having nitrogen atom include derivatives having benzimidazole ring, derivatives having benzotriazole ring, derivatives having pyridinoimidazole ring, derivatives having pyrimidinoimidazole ring and derivatives having pyridazinoimidazole ring. As the five-membered cyclic derivative having nitrogen atom, derivatives represented by the following general formula (B) are preferable:

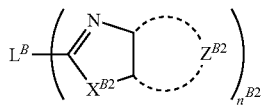
(B)

In general formula (B), $L^B$ represents a bonding group having a valence of two or greater. Examples of the bonding group include carbon, silicon, nitrogen, boron, oxygen, sulfur, metals (such as barium and beryllium), aromatic hydrocarbon rings and aromatic heterocyclic rings. Among these bonding groups, carbon atom, nitrogen atom, silicon atom, boron atom, oxygen atom, sulfur atom, aryl groups and aromatic heterocyclic group are preferable, and carbon atom, silicon atom, aryl groups and aromatic heterocyclic groups are more preferable.

The group represented by $L^B$ may have substituents. As the substituent, alkyl groups, alkenyl groups, alkynyl groups, aryl groups, amino groups, alkoxyl groups, aryloxyl groups, acyl groups, alkoxycarbonyl groups, aryloxycarbonyl groups, acyloxyl groups, acylamino groups, alkoxycarbonylamino groups, aryloxycarbonylamino groups, sulfonylamino group, sulfamoyl group, carbamoyl group, alkylthio groups, arylthio groups, sulfonyl group, halogen atoms, cyano group and aromatic heterocyclic groups are preferable; alkyl groups, aryl groups, alkoxyl groups, aryloxyl groups, halogen atoms, cyano group and aromatic heterocyclic groups are more preferable; alkyl groups, aryl groups, alkoxyl groups, aryloxyl groups and aromatic heterocyclic groups are still more preferable; and alkyl groups, aryl groups, alkoxyl groups, aryloxyl groups and aromatic heterocyclic groups are most preferable.

Examples of the bonding group represented by $L^B$ include groups shown in the following:

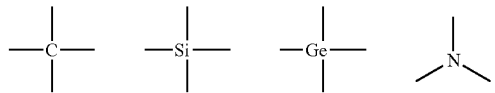

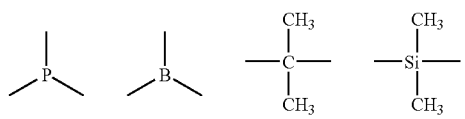

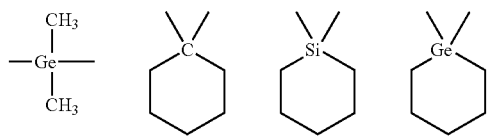

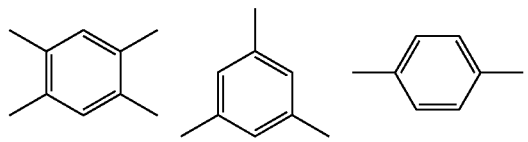

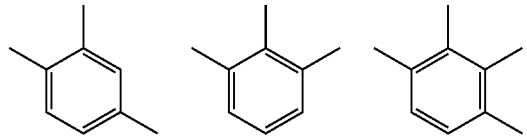

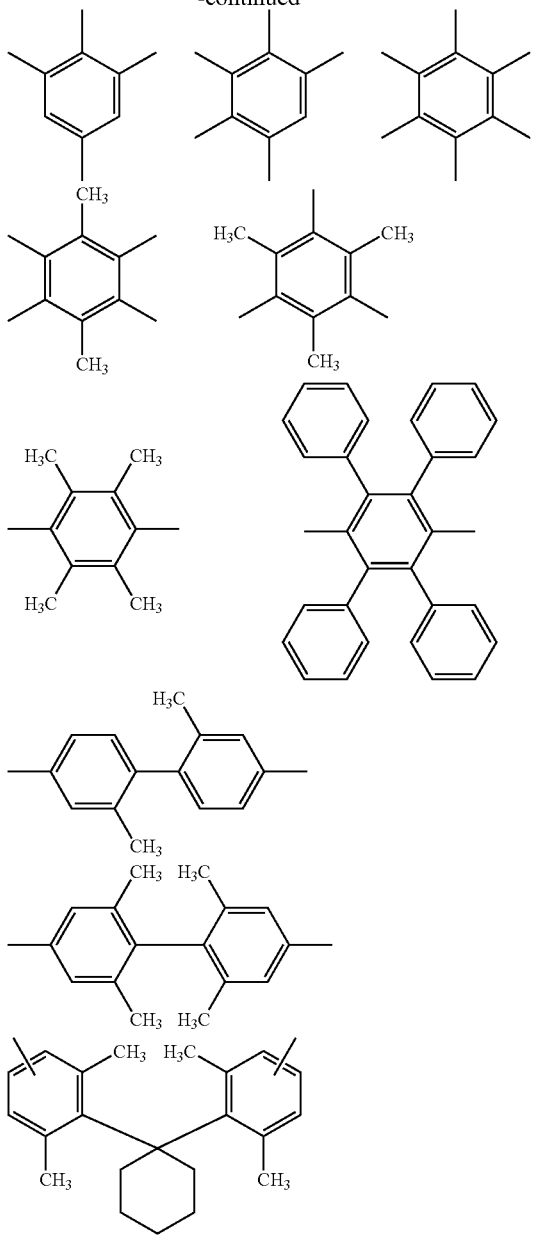

In general formula (B), $X^{B2}$ represents —O—, —S— or a group represented by =N—$R^{B2}$. $R^{B2}$ represents hydrogen atom, an aliphatic hydrocarbon group, an aryl group or a heterocyclic group.

The aliphatic hydrocarbon group represented by $R^{B2}$ is a linear, branched or cyclic alkyl group (an alkyl group preferably having 1 to 20 carbon atoms, more preferably having 1 to 12 carbon atoms and most preferably having 1 to 8 carbon atoms, such as methyl group, ethyl group, isopropyl group, t-butyl group, n-octyl group, n-decyl group, n-hexadecyl group, cyclopropyl group, cyclopentyl group and cyclohexyl group), an alkenyl group (an alkenyl group preferably having 2 to 20 carbon atoms, more preferably having 2 to 12 carbon atoms and most preferably having 2 to 8 carbon atoms, such as vinyl group, allyl group, 2-butenyl group and 3-pentenyl group) or an alkynyl group (an alkynyl group preferably having 2 to 20 carbon atoms, more preferably having 2 to 12 carbon atoms and most preferably having 2 to 8 carbon atoms, such as propargyl group and 3-pentynyl group) and is preferably an alkyl group.

The aryl group represented by $R^{B2}$ is an aryl group having a single ring or condensed rings, which preferably has 6 to 30 carbon atoms, more preferably has 6 to 20 carbon atoms and most preferably has 6 to 12 carbon atoms, such as phenyl group, 2-methylphenyl group, 3-methylphenyl group, 4-methylphenyl group, 2-methoxyphenyl group, 3-trifluoromethylphenyl group, pentafluorophenyl group, 1-naphthyl group and 2-naphthyl group.

The heterocyclic group represented by $R^{B2}$ is a heterocyclic group having a single ring or condensed rings, which preferably has 1 to 20 carbon atoms, more preferably has 1 to 12 carbon atoms and most preferably has 2 to 10 carbon atoms, and is preferably an aromatic heterocyclic group having at least one of nitrogen atom, oxygen atom, sulfur atom and selenium atom. Examples of the heterocyclic group include groups derived from pyrrolidine, piperidine, piperazine, morpholine thiophene, selenophene, furan, pyrrol, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthylidine, quinoxaline, quinazoline, cinnoline, pteridine, acridine, phenanthroline, phenazine, tetrazole, benzimidazole, benzoxazole, benzothiazole, benzotriazole, tetrazaindene, carbazole and azepine; preferably groups derived from furan, thiophene, pyridine, pyrazine, pyrimidine, pyridazine, triazine, quinoline, phthalazine, naphthylidine, quinoxaline and quinazoline; more preferably groups derived from furan, thiophene, pyridine and quinoline; and most preferably groups derived from quinoline.

The aliphatic hydrocarbon group, the aryl group and the heterocyclic group represented by $R^{B2}$ may have substituents. Examples of the substituent include the substituents described above as the examples of the substituent to the group represented by $L^B$, and preferable examples of the substituent include the substituents described above as the preferable examples of the substituent to the group represented by $L^B$.

As the group represented by $R^{B2}$, aliphatic hydrocarbon groups, aryl groups and heterocyclic groups are preferable, aliphatic hydrocarbon groups (preferably the groups having 6 to 30 carbon atoms, more preferably the groups having 6 to 20 carbon atoms and most preferably the groups having 6 to 12 carbon atoms) and aryl groups are more preferable, and aliphatic hydrocarbon groups (preferably having 1 to 20 carbon atoms, more preferably having 1 to 12 carbon atoms and most preferably having 2 to 10 carbon atoms) are most preferable.

$X^{B-2}$ preferably represents —O— or a group represented by =N—$R^{B2}$, more preferably a group represented by =N—$R^{B2}$, and most preferably a group represented by =N—$R^{B2}$.

$Z^{B2}$ represents a group of atoms necessary for forming an aromatic ring. The aromatic ring formed with the group of atoms represented by $Z^{B2}$ may be any of an aromatic hydrocarbon ring and an aromatic heterocyclic ring. Examples of the aromatic ring include benzene ring, pyridine ring, pyrazine ring, pyrimidine ring, pyridazine ring, triazine ring, pyrrol ring, furan ring, thiophene ring, selenophene ring, tellurophene ring, imidazole ring, thiazole ring, selenazole ring, tellurazole ring, thiadiazole ring, oxadiazole ring and pyrazole ring. Among these rings, benzene ring, pyridine ring, pyrazine ring, pyrimidine ring and pyridazine ring are preferable, benzene ring, pyridine ring and pyrazine ring are more preferable, benzene ring and pyridine ring are still more preferable, and pyridine ring is most preferable.

The aromatic ring formed with the group of atoms represented by $Z^{B2}$ may form a condensed ring in combination with other rings and may have substituents. Examples of the substituent include the substituents described above as the examples of the substituent to the groups represented by $L^B$. Preferable examples of the substituent include alkyl groups, alkenyl groups, alkynyl groups, aryl groups, amino groups, alkoxyl groups, aryloxyl groups, acyl groups, alkoxycarbonyl groups, aryloxycarbonyl groups, acyloxyl groups, acylamino groups, alkoxycarbonylamino groups, aryloxycarbonylamino groups, sulfonylamino group, sulfamoyl group, carbamoyl group, alkylthio groups, arylthio groups, sulfonyl group, halogen atoms, cyano group and heterocyclic groups; more preferably, alkyl groups, aryl groups, alkoxyl groups, aryloxyl groups, halogen atoms, cyano group and heterocyclic groups; still more preferably, alkyl groups, aryl groups, alkoxyl groups, aryloxyl groups and aromatic heterocyclic groups; and most preferably alkyl groups, aryl groups, alkoxyl groups and aromatic heterocyclic groups.

$n^{B2}$ represents an integer of 1 to 4 and preferably 2 or 3.

Among the five-membered cyclic derivative having nitrogen atom represented by the above general formula (B), derivatives represented by the following general formula (B') are preferable.

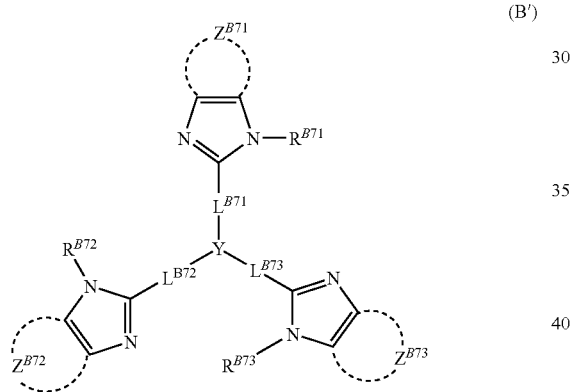

(B')

In general formula (B'), $R^{B71}$, $R^{B72}$ and $R^{B73}$ are each as defined for $R^{B2}$ in general formula (B), and the preferable groups are the same as the preferable groups represented by $R^{B2}$.

$Z^{B71}$, $Z^{B72}$ and $Z^{B73}$ are each as defined for $Z^{B2}$ in general formula (B), and the preferable groups are the same as the groups described for $Z^{B2}$.

$L^{B71}$, $L^{B72}$ and $L^{B73}$ each represent a bonding group. Examples of the group include divalent groups derived from the groups described as the examples of the group represented by $L^B$ in general formula (B). The bonding group is preferably the single bond, a divalent aromatic hydrocarbon cyclic group, a divalent aromatic heterocyclic group or a bonding group obtained as a combination of these groups, and more preferably the single bond. The groups represented by $L^{B71}$, $L^{B72}$ and $L^{B73}$ may have substituents. Examples of the substituent include the substituents described above as the examples of the substituent to the groups represented by $L^B$ in general formula (B). Preferable examples of the substituent include the substituents described above as the preferable examples of the substituent to the groups represented by $L^B$.

Y represents nitrogen atom, 1,3,5-benzenetriyl group or 2,4,6-triazinetriyl group. 1,3,5-Benzenetriyl group may have substituents at the 2-, 4- and 6-positions. Examples of the substituent include alkyl groups, aromatic hydrocarbon cyclic groups and halogen atoms.

Specific examples of the five-membered cyclic derivatives having nitrogen atom represented by general formulae (B) and (B') are shown in the following. However, the five-membered cyclic derivative having nitrogen atom is not limited to the derivatives shown as the examples.

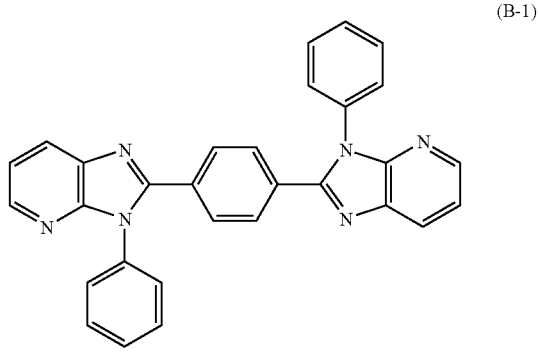

(B-1)

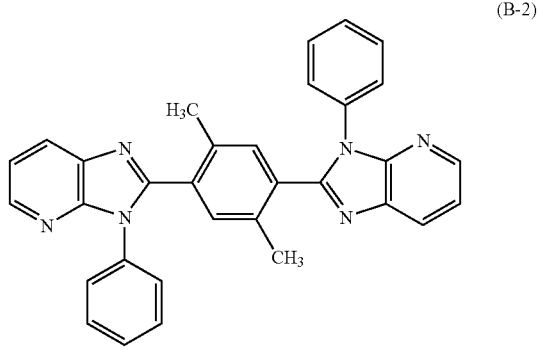

(B-2)

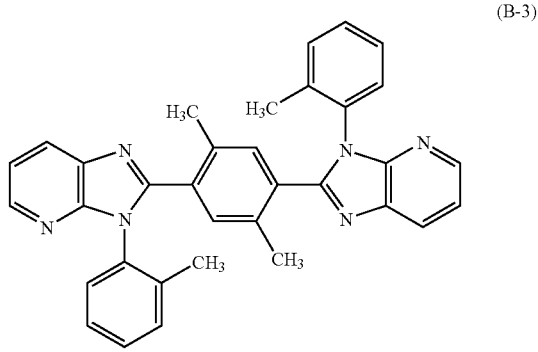

(B-3)

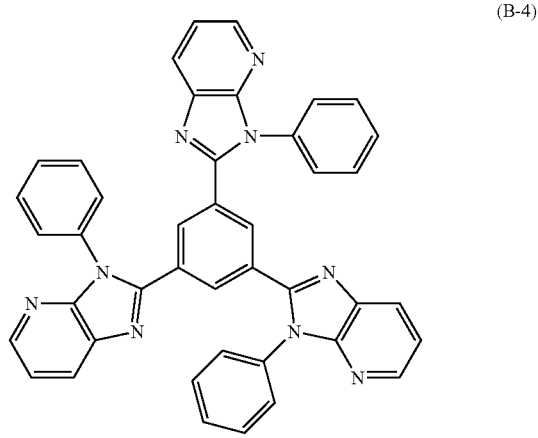

(B-4)

-continued
(B-5)
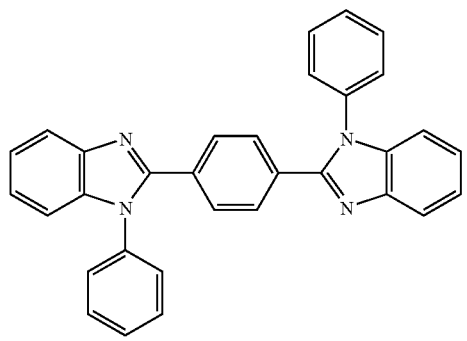
(B-6)
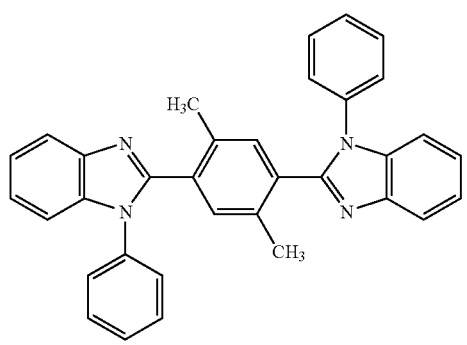
(B-7)
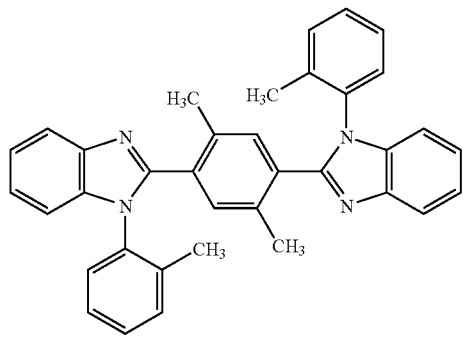
(B-8)
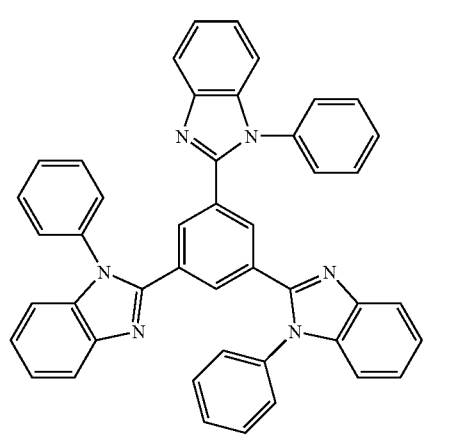
-continued
(B-9)
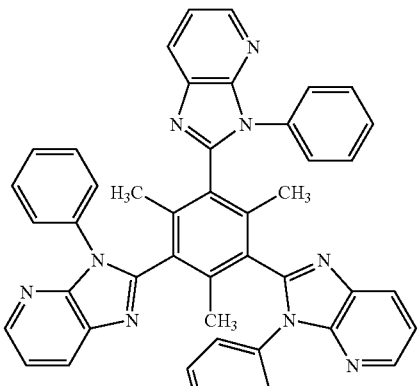
(B-10)
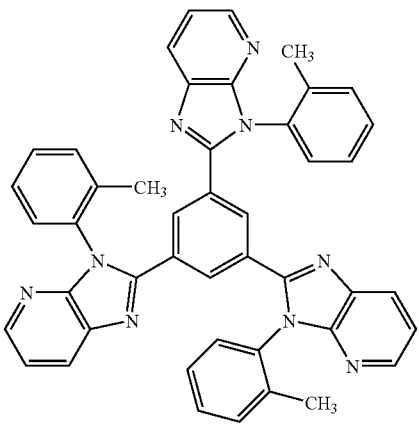
(B-11)
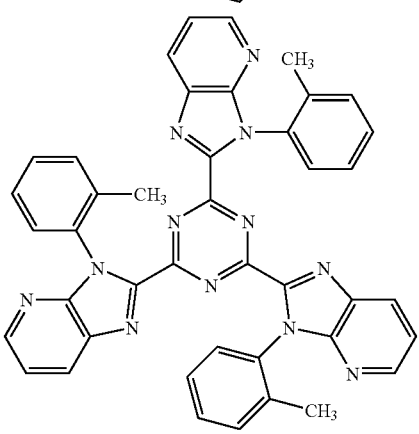
(B-12)
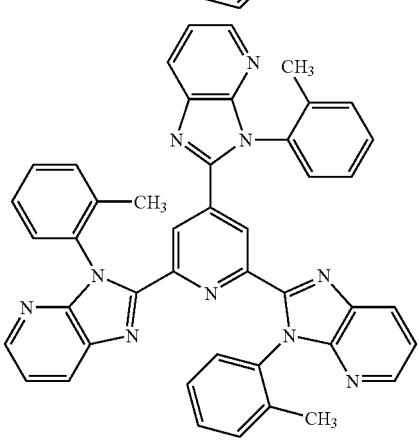

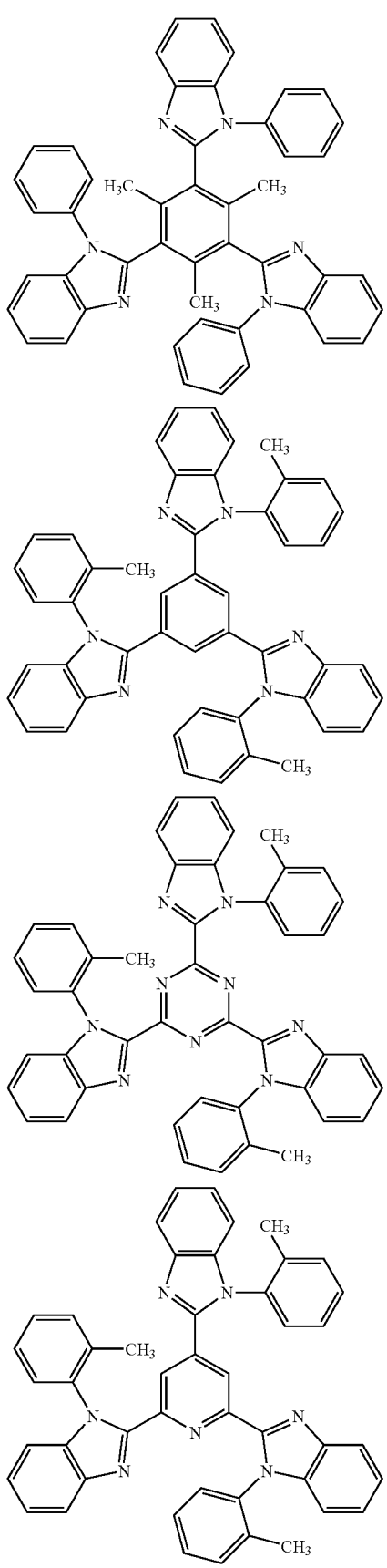

(B-13)

(B-14)

(B-15)

(B-16)

Examples of the compound constituting the electron injecting layer and the electron transporting layer other than the material for organic EL devices of the present invention include compounds having a structure of a combination of an electron deficient five-membered cyclic skeleton structure having nitrogen or an electron deficient six-membered cyclic skeleton structure having nitrogen and a substituted or unsubstituted indole skeleton structure, a substituted or unsubstituted carbazole skeleton structure or a substituted or unsubstituted azacarbazole skeleton structure. Preferable examples of the electron deficient five-membered cyclic skeleton structure having nitrogen and the electron deficient six-membered cyclic skeleton structure having nitrogen include structures such as skeleton structures of pyridine, pyrimidine, pyrazine, triazine, triazole, oxadiazole, pyrazole, imidazole, quinoxaline and pyrrol and molecular skeleton structures formed by condensation of these skeleton structures such as the skeleton structures of benzimidazole and imidazopyridine. Examples of the combination of the skeleton structures include combinations of the skeleton structure of pyridine, pyrimidine, pyrazine or triazine and the skeleton structure of carbazole, indole, azacarbazole or quinoxaline. The above skeleton structure may be substituted or unsubstituted.

Examples of the electron transporting compound is shown in the following.

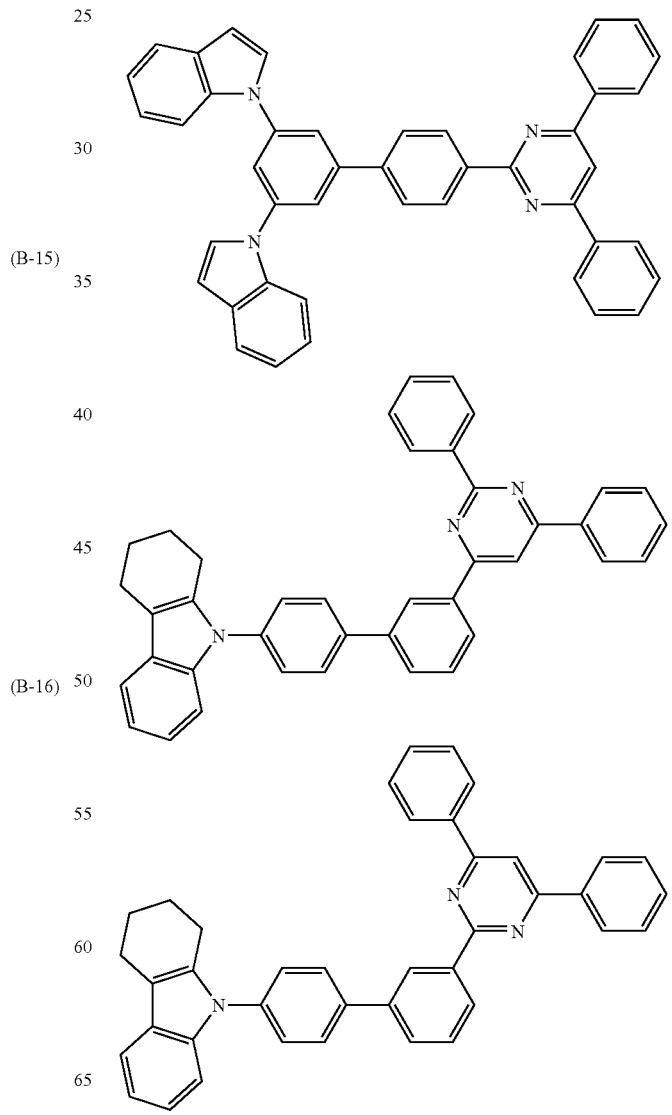

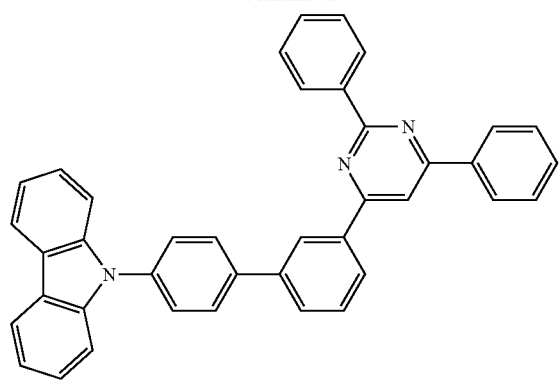
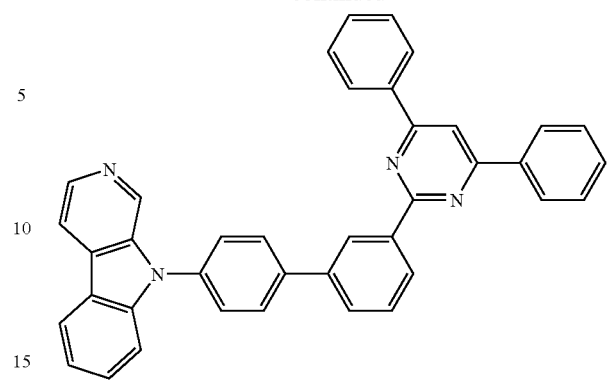
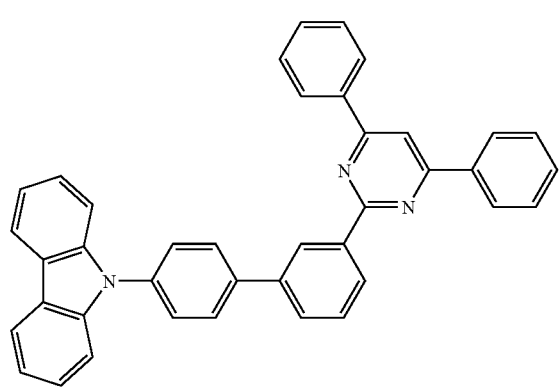
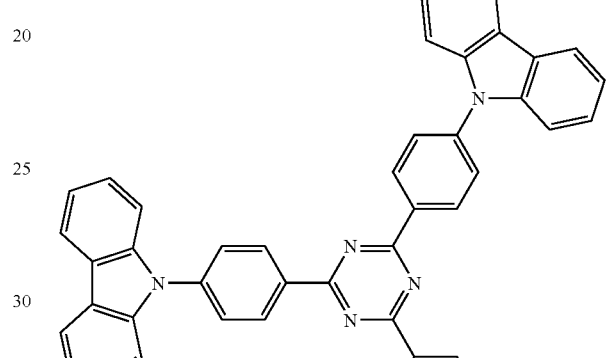
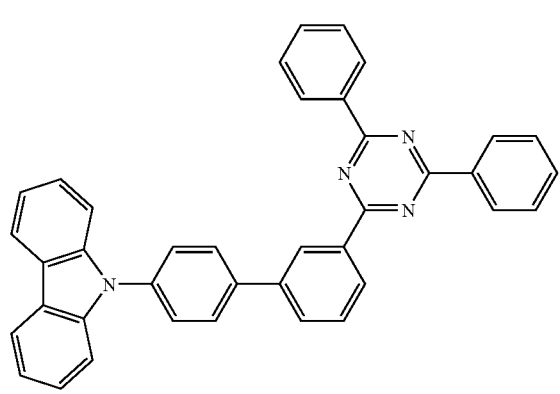
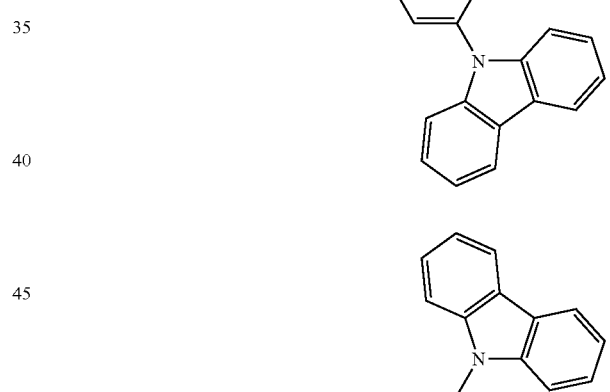
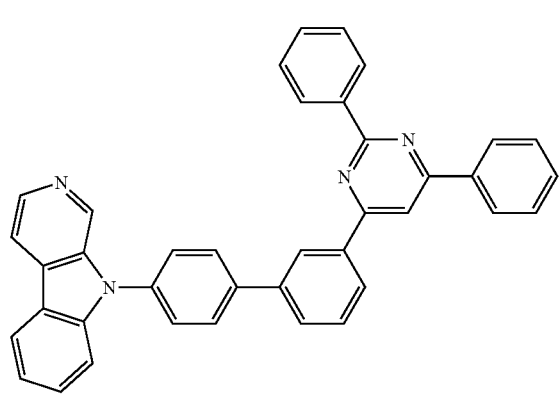
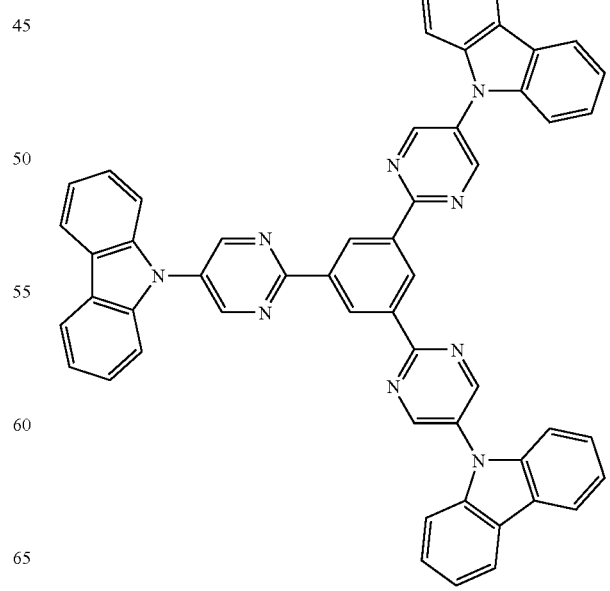

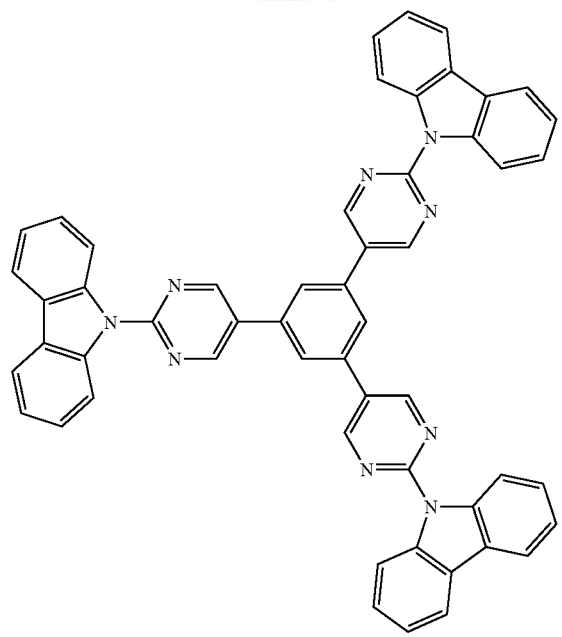
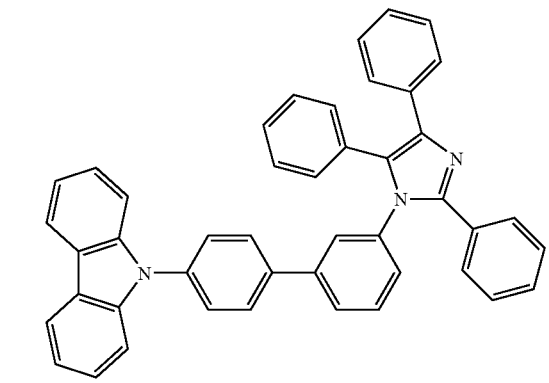
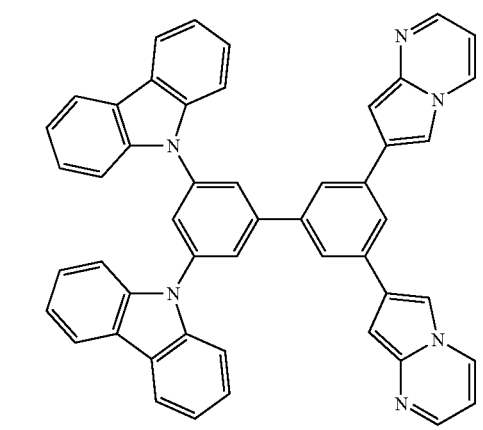
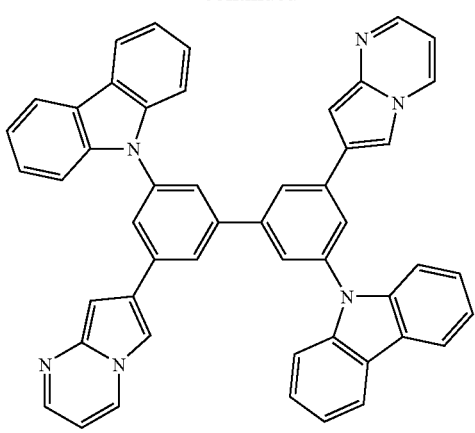
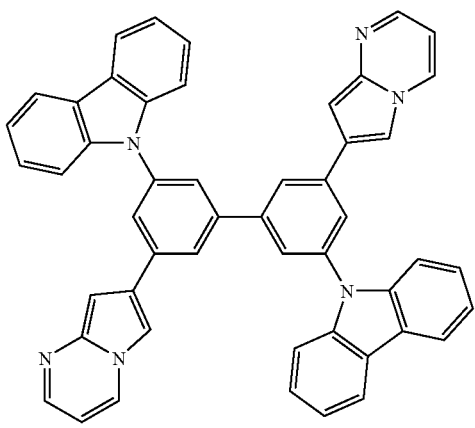
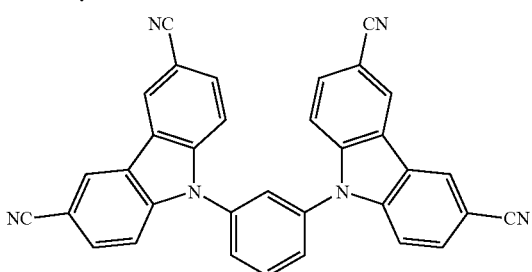
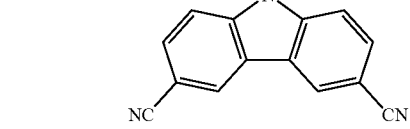
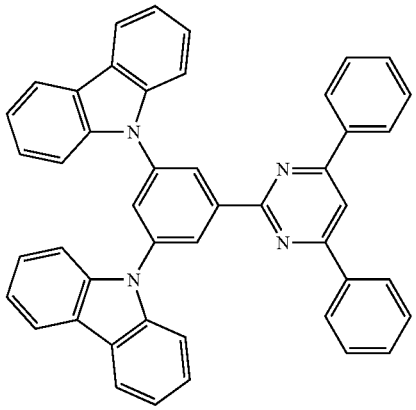

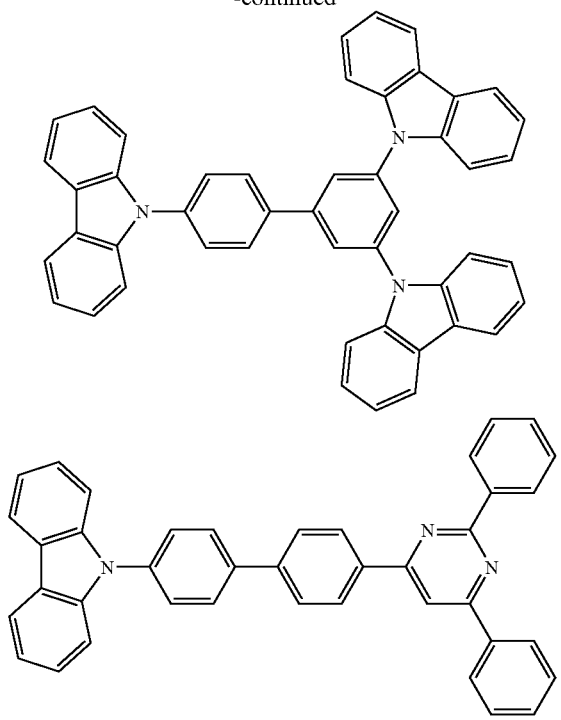

The electron injecting layer and the electron transporting layer may have a single layer structure comprising one or more types of the above material or a multilayer structure comprising a plurality of layers having the same composition or different compositions. It is preferable that the above layer comprises a compound having a π-electron deficient heterocyclic group having nitrogen atom.

It is preferable that, as the component constituting the electron injecting layer, an insulating material or a semiconductor of an inorganic compound is used in combination with the cyclic derivative having nitrogen atom described above. When the electron injecting layer comprises an insulating material or a semiconductor, leak of the electric current can be effectively prevented, and the electron injecting property can be improved.

As the insulating material, it is preferable that at least one metal compound selected from the group consisting of chalcogenides of alkali metals, chalcogenides of alkaline earth metals, halides of alkali metals and halides of alkaline earth metals is used. It is more preferable that the electron injecting layer comprises the above chalcogenide of an alkali metal since the electron injecting property can be further improved. Preferable examples of the chalcogenide of an alkali metal include $Li_2O$, $K_2O$, $Na_2S$, $Na_2Se$ and $Na_2O$. Preferable examples of the chalcogenide of an alkaline earth metal include CaO, BaO, SrO, BeO, BaS and CaSe. Preferable examples of the halide of an alkali metal include LiF, NaF, KF, LiCl, KCl and NaCl. Preferable examples of the halide of an alkaline earth metal include fluoride such as $CaF_2$, $BaF_2$, $SrF_2$, $MgF_2$ and $BeF_2$ and halides other than the fluorides.

Examples of the semiconductor include oxides, nitrides and oxide nitrides comprising at least one element selected from Ba, Ca, Sr, Yb, Al, Ga, In, Li, Na, Cd, Mg, Si, Ta, Sb and Zn singly or in combination of two or more. It is preferable that the inorganic compound constituting the electron injecting layer forms a finely crystalline or amorphous insulating thin film. When the electron injecting layer is constituted with the insulating thin film described above, a more uniform thin film can be formed, and defects of pixels such as dark spots can be decreased. Examples of the inorganic compound include chalcogenides of alkali metals, chalcogenides of alkaline earth metals, halides of alkali metals and halides of alkaline earth metals which are described above.

In the organic EL device of the present invention, it is preferable that the electron injecting layer comprises a reducing dopant described above.

In the present invention, the anode in the organic EL device plays the role of injecting holes into the hole transporting layer or the light emitting layer. It is effective that the anode has a work function of 4.5 eV or greater. Examples of the material for the anode used in the present invention include indium tin oxide alloys (ITO), tin oxide (NESA), gold, silver, platinum and copper. For the cathode, a material having a small work function is preferable so that electron can be injected into the electron injecting layer or the light emitting layer. The material for the cathode is not particularly limited. Specifically, indium, aluminum, magnesium, magnesium-indium alloys, magnesium-aluminum alloys, aluminum-lithium alloys, aluminum-scandium-lithium alloys and magnesium-silver alloys can be used.

The process for forming the layers in the organic EL devices of the present invention is not particularly limited, and a conventional process for forming a layer such as the vacuum vapor deposition process and the spin coating process can be used. The organic thin film layer comprising the compound represented by general formula (1) or (2), which is used for the organic EL device of the present invention, can be formed in accordance with a conventional process, examples of which include the vacuum vapor deposition process, the molecular beam epitaxy process (the MBE process) and coating processes using a solution in a solvent such as the dipping process, the spin coating process, the casting process, the bar coating process and the roll coating process.

The thickness of each organic layer in the organic EL device of the present invention is not particularly limited. In general, an excessively small thickness tends to form defects such as pin holes, and an excessively great thickness requires application of a high voltage to decrease the efficiency. In general, it is preferable that the thickness is in the range of several nm to 1 μm.

EXAMPLES

The present invention will be described more specifically with reference to examples in the following.

Synthesis Example 1

Synthesis of Compound A-2

Compound A-2 was synthesized in accordance with the route of synthesis shown in the following:

Intermediate Compound A

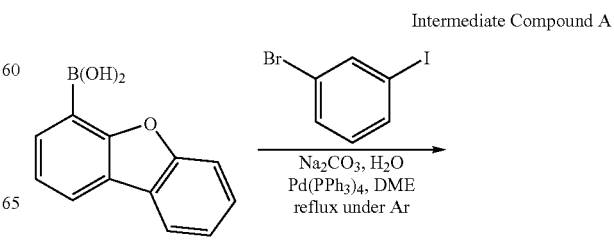

-continued

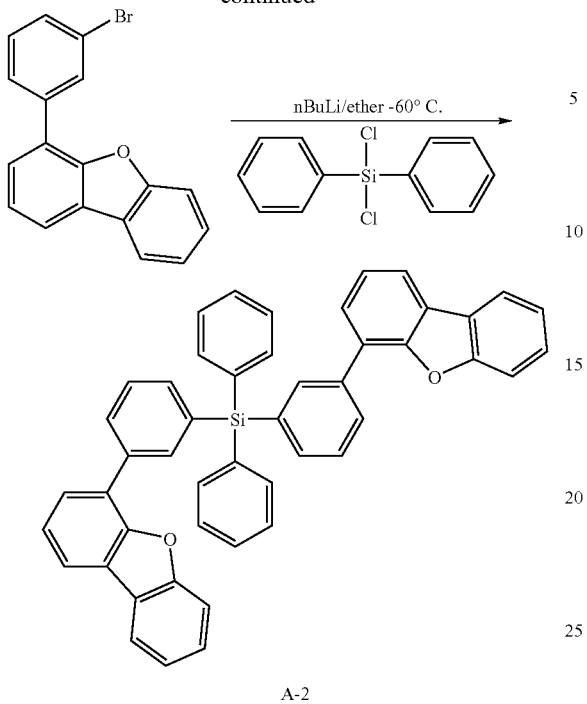

A-2

Into a flask, 3.12 g of 4-dibenzofuranboronic acid, 4.07 g of 1-bromo-3-iodobenzene, 0.33 g of tetrakis-triphenylphosphinepalladium(0), 25 g of a 2M aqueous solution of sodium carbonate and 70 ml of dimethoxyethane were placed, and the resultant mixture was heated under the refluxing condition for 8 hours under the atmosphere of argon. After it was confirmed in accordance with the thin layer chromatography (TLC) that the reaction had been completed, dichloromethane was added. The obtained mixture was washed with water and a saturated aqueous solution of sodium chloride, and the organic layer was separated. The organic layer was dried with magnesium sulfate, filtered and concentrated, and a yellow oily substance was obtained. After purification in accordance with the column chromatography, 4.13 g of a white solid substance was obtained (the yield: 89%; Intermediate Compound A). The result of the field desorption mass analysis (FD-MS) on the obtained substance is shown in the following.

FD-MS: calcd.: $C_{18}H_{11}BrO$ 323.18. found: 323.

The entire amount of Intermediate Compound A obtained above was placed into a flask. Then, 40 ml of dehydrated diethyl ether and 30 ml of dehydrated tetrahydrofuran were added under the atmosphere of argon, and Intermediate Compound A was dissolved under stirring. The resultant solution was cooled at −60° C. in a MeOH-dry ice bath. To the cooled solution, 10 ml of a 1.6 M hexane solution of normal-butyllithium was added dropwise using a syringe. After the resultant solution was stirred for 15 minutes, a solution prepared by dissolving 1.35 g of dichlorodiphenylsilane into 10 ml of dehydrated tetrahydrofuran was added dropwise. The temperature was elevated at 5° C. and, after it was confirmed in accordance with TLC that the reaction had been completed, the reaction was terminated by adding a saturated aqueous solution of ammonium chloride. After dichloromethane was added, the obtained mixture was washed with water and a saturated aqueous solution of sodium chloride, and the organic layer was separated. The solution was dried with magnesium sulfate, filtered and concentrated, and a colorless oily substance was obtained. After purification in accordance with the column chromatography, a white solid substance was obtained. The obtained substance was washed with hexane and dried, and 2.42 g of Compound A-2 was obtained (the yield: 56%). The result of FD-MS on the obtained substance is shown in the following.

FD-MS: calcd.: $C_{48}H_{32}O_2Si$ 668.85. found: 668.

The obtained Compound A-2 was purified by sublimation at 320° C. under $1.3\times10^{-2}$ Torr and used for the vapor deposition. The purity was 99.5% in accordance with the high performance liquid chromatography (HPLC).

Synthesis Example 2

Synthesis of Compound B-1

Compound B-1 was synthesized in accordance with the route of synthesis shown in the following:

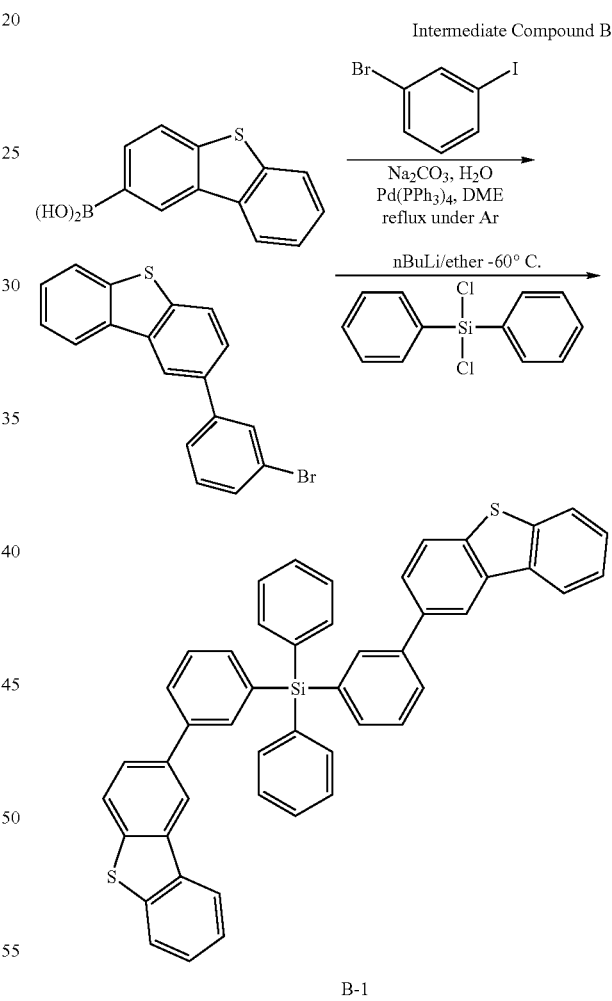

B-1

Into a flask, 3.3 g of 2-dibenzothiopheneboronic acid, 4.0 g of 1-bromo-3-iodobenzene, 0.31 g of tetrakis-triphenylphosphinepalladium(0), 25 ml of a 2M aqueous solution of sodium carbonate and 70 ml of dimethoxyethane were placed, and the resultant mixture was heated under the refluxing condition for 9 hours under the atmosphere of argon. After it was confirmed in accordance with TLC that the reaction had been completed, dichloromethane was added. The obtained mixture was washed with water and a saturated aqueous solution of sodium chloride, and the organic layer was separated. The organic layer was dried with magnesium sulfate, filtered and concentrated, and a yellow oily substance was obtained. After purification in accordance with the column chromatography, 3.96 g of a white solid substance was obtained (the yield: 83%; Intermediate Compound B). The result of FD-MS on the obtained substance is shown in the following.

FD-MS: calcd.: $C_{18}H_{11}BrS$ 339.25. found: 339.

Intermediate Compound B obtained above in an amount of 3.96 g was placed into a flask. Then, 40 ml of dehydrated tetrahydrofuran was added under the atmosphere of argon, and Intermediate Compound B was dissolved under stirring. The resultant solution was cooled at −70° C. in a MeOH-dry ice bath. To the cooled solution, 8 ml of a 1.6 M hexane solution of normal-butyllithium was added dropwise using a syringe. After the resultant solution was stirred for 15 minutes, a solution prepared by dissolving 1.35 ml of dichlorodiphenylsilane into 10 ml of dehydrated tetrahydrofuran was added dropwise. The temperature was elevated at 5° C. and, after it was confirmed in accordance with TLC that the reaction had been completed, the reaction was terminated by adding a saturated aqueous solution of ammonium chloride. After dichloromethane was added, the obtained mixture was washed with water and a saturated aqueous solution of sodium chloride, and the organic layer was separated. The solution was dried with magnesium sulfate, filtered and concentrated, and a colorless oily substance was obtained. After purification in accordance with the column chromatography, a white solid substance was obtained. The obtained substance was washed with hexane three times and dried, and 2.49 g of Compound B-1 was obtained (the yield: 68%). The result of FD-MS on the obtained substance is shown in the following.

FD-MS: calcd.: $C_{48}H_{32}S_2Si$ 700.98. found: 700

The obtained Compound B-1 was purified by sublimation at 310° C. under $5.0 \times 10^{-6}$ Torr and used for the vapor deposition. The purity was 99.3% in accordance with HPLC.

Synthesis Example 3

Synthesis of Compound B-2

Compound B-2 was synthesized in accordance with the route of synthesis shown in the following:

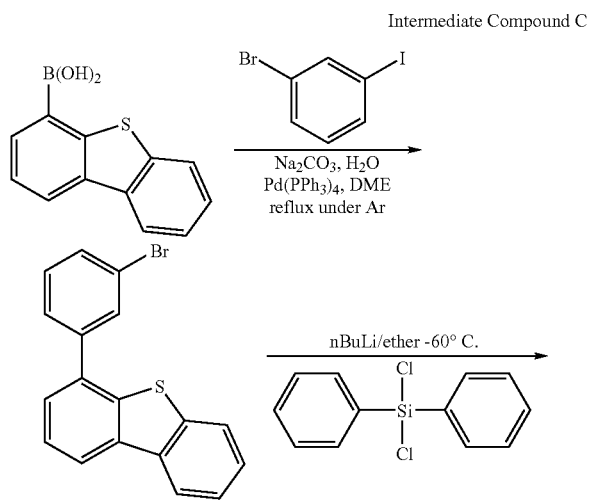

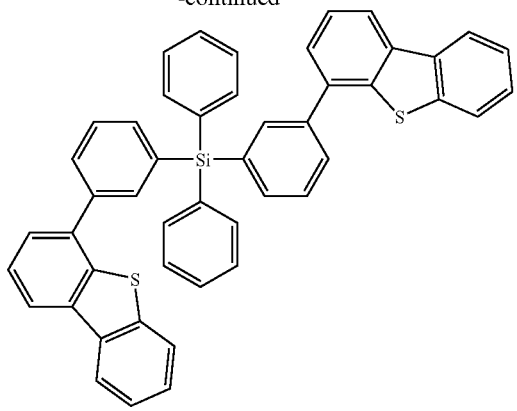

B-2

Into a flask, 3.3 g of 4-dibenzothiopheneboronic acid, 4.0 g of 1-bromo-3-iodobenzene, 0.31 g of tetrakis-triphenylphosphinepalladium(0), 25 ml of a 2M aqueous solution of sodium carbonate and 70 ml of dimethoxyethane were placed, and the resultant mixture was heated under the refluxing condition for 9 hours under the atmosphere of argon. After it was confirmed in accordance with TLC that the reaction had been completed, dichloromethane was added. The obtained mixture was washed with water and a saturated aqueous solution of sodium chloride, and the organic layer was separated. The organic layer was dried with magnesium sulfate, filtered and concentrated, and a yellow oily substance was obtained. After purification in accordance with the column chromatography, 4.2 g of a white solid substance was obtained (the yield: 88%; Intermediate Compound C). The result of FD-MS on the obtained substance is shown in the following.

FD-MS: calcd.: $C_{18}H_{11}BrS$ 339.25. found: 339

Intermediate Compound C obtained above in an amount of 4.0 g was placed into a flask. Then, 40 ml of dehydrated tetrahydrofuran was added under the atmosphere of argon, and Intermediate Compound C was dissolved under stirring. The resultant solution was cooled at −70° C. in a MeOH-dry ice bath. To the cooled solution, 8 ml of a 1.6 M hexane solution of normal-butyllithium was added dropwise using a syringe. After the resultant solution was stirred for 15 minutes, a solution prepared by dissolving 1.4 ml of dichlorodiphenylsilane into 10 ml of dehydrated tetrahydrofuran was added dropwise. The temperature was elevated at 5° C. and, after it was confirmed in accordance with TLC that the reaction had been completed, the reaction was terminated by adding a saturated aqueous solution of ammonium chloride. After dichloromethane was added, the obtained mixture was washed with water and a saturated aqueous solution of sodium chloride, and the organic layer was separated. The solution was dried with magnesium sulfate, filtered and concentrated, and a colorless oily substance was obtained. After purification in accordance with the column chromatography, a white solid substance was obtained. The obtained substance was washed with hexane three times and dried, and 2.52 g of Compound B-2 was obtained (the yield: 69%). The result of FD-MS on the obtained substance is shown in the following.

FD-MS: calcd.: $C_{48}H_{32}S_2Si$ 700.98. found: 700

The obtained Compound B-2 was purified by sublimation at 310° C. under $5.5 \times 10^{-6}$ Torr and used for the vapor deposition. The purity was 99.3% in accordance with HPLC.

Synthesis Example 4

Synthesis of Compound C-2

Compound C-2 was synthesized in accordance with the route of synthesis shown in the following:

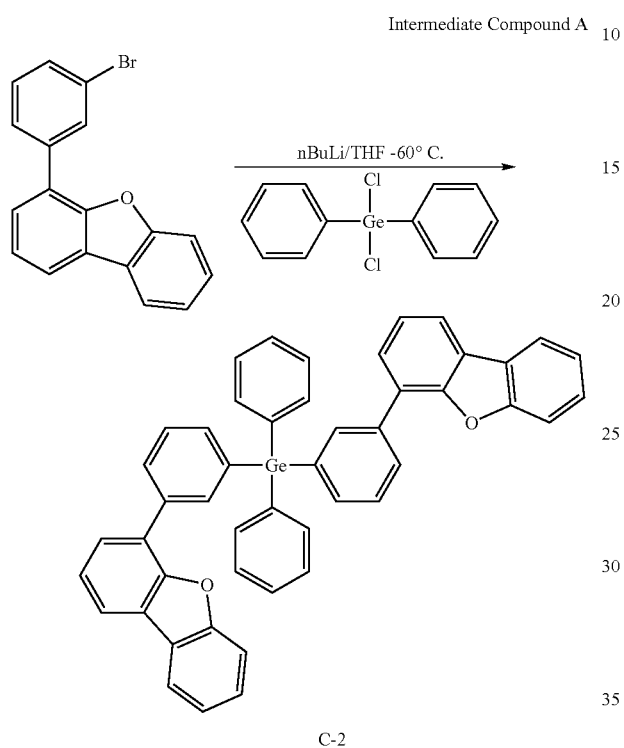

Intermediate Compound A in an amount of 2.48 g was placed into a flask. Then, 30 ml of dehydrated tetrahydrofuran was added under the atmosphere of argon, and Intermediate Compound A was dissolved under stirring. The resultant solution was cooled at −60° C. in a MeOH-dry ice bath. To the cooled solution, 5 ml of a 1.6 M hexane solution of normal-butyllithium was added dropwise using a syringe. After the resultant solution was stirred for 15 minutes, a solution prepared by dissolving 1.0 g of diphenyldichlorogermane into 13 ml of dehydrated tetrahydrofuran was added dropwise. The temperature was elevated at 5° C. and, after it was confirmed in accordance with TLC that the reaction had been completed, the reaction was terminated by adding a saturated aqueous solution of ammonium chloride. After dichloromethane was added, the obtained mixture was washed with water and a saturated aqueous solution of sodium chloride, and the organic layer was separated. The solution was dried with magnesium sulfate, filtered and concentrated, and a colorless oily substance was obtained. After purification in accordance with the column chromatography, a white solid substance was obtained. The obtained substance was washed with hexane and dried, and 1.61 g of Compound C-2 was obtained (the yield: 67%). The result of FD-MS on the obtained substance is shown in the following.

FD-MS: calcd.: $C_{48}H_{32}O_2Ge$ 713.41. found: 713

The obtained Compound C-2 was purified by sublimation at 340° C. under $1.9 \times 10^{-3}$ Torr and used for the vapor deposition. The purity was 99.7% in accordance with HPLC.

Synthesis Example 5

Synthesis of Compound C-7

Compound C-7 was synthesized in accordance with the route of synthesis shown in the following:

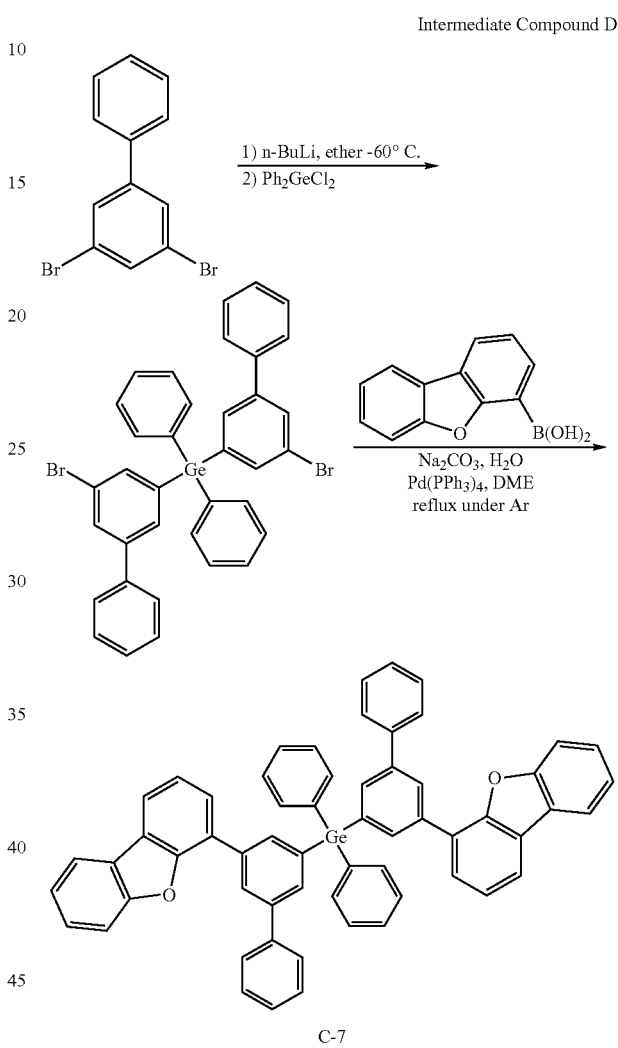

3,5-Dibromobiphenyl in an amount of 3.08 g was placed into a flask. Then, 40 ml of dehydrated diethyl ether was added under the atmosphere of argon, and 3,5-dibromobiphenyl was dissolved under stirring. The resultant solution was cooled at −60° C. in a MeOH-dry ice bath. To the cooled solution, 6.2 ml of a 1.6 M hexane solution of normal-butyllithium was added dropwise using a syringe. After the temperature was elevated at −10° C., the temperature was lowered at −40° C., and a solution prepared by dissolving 1.36 g of diphenyldichlorogermane into 10 ml of dehydrated diethyl ether was added dropwise. The temperature was elevated at −10° C. and, after it was confirmed in accordance with TLC that the reaction had been completed, the reaction was terminated by adding a saturated aqueous solution of ammonium chloride. After dichloromethane was added, the obtained mixture was washed with water, and the organic layer was separated. The solution was dried with magnesium sulfate, filtered and concentrated, and a yellow oily substance was obtained. After purification in accordance with the column chromatography, a white solid substance was obtained. The obtained substance was washed with hexane and dried, and 2.85 g of Intermediate Compound D was obtained (the yield: 90%). The result of FD-MS on the obtained substance is shown in the following.

FD-MS: calcd.: $C_{36}H_{26}Br_2Ge$ 691.01. found: 691

Intermediate Compound D obtained above in an amount of 2.85 g, i.e., the entire amount, 1.85 g of 4-dibenzofuranboronic acid, 0.19 g of tetrakis-triphenylphosphinepalladium (0), 19 g of a 2M aqueous solution of sodium carbonate and 50 ml of dimethoxyethane were placed into a flask, and the resulting mixture was heated under the refluxing condition under the atmosphere of argon for 9 hours. After it was confirmed in accordance with TLC that the reaction had been completed, dichloromethane was added. The obtained mixture was washed with water and a saturated aqueous solution of sodium chloride, and the organic layer was separated. The organic layer was dried with magnesium sulfate, filtered and concentrated, and an orange oily substance was obtained. After purification in accordance with the column chromatography, 2.86 g of Compound C-7 was obtained as a white solid substance (the yield: 80%). The result of FD-MS on the obtained substance is shown in the following.

FD-MS: calcd.: $C_{62}H_{40}GeO_2$ 865.60. found: 865

The obtained Compound B-2 was purified by sublimation at 360° C. under 3.7×10$^{-6}$ Torr and used for the vapor deposition. The purity was 99.1% in accordance with HPLC.

Synthesis Example 6

Synthesis of Compound D-2

Compound D-2 was synthesized in accordance with the route of synthesis shown in the following:

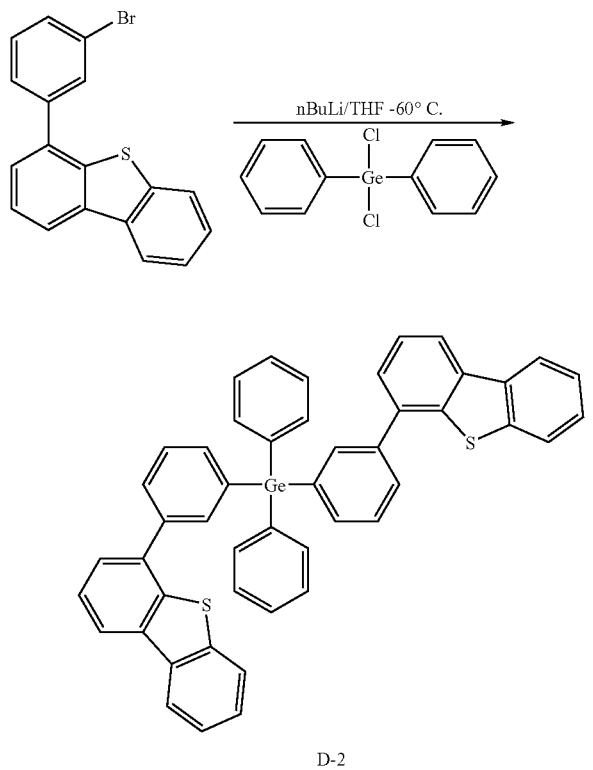

D-2

Intermediate Compound C in an amount of 2.57 g was placed into a flask. Then, 30 ml of dehydrated tetrahydrofuran was added under the atmosphere of argon, and Intermediate Compound C was dissolved under stirring. The resultant solution was cooled at −70° C. in a MeOH-dry ice bath. To the cooled solution, 5 ml of a 1.6 M hexane solution of normal-butyllithium was added dropwise using a syringe. After the resultant solution was stirred for 15 minutes, a solution prepared by dissolving 1.0 g of dichlorodiphenylgermane into 15 ml of dehydrated tetrahydrofuran was added dropwise. The temperature was elevated at −12° C. and, after it was confirmed in accordance with TLC that the reaction had been completed, the reaction was terminated by adding a saturated aqueous solution of ammonium chloride. After dichloromethane was added, the obtained mixture was washed with water, and the organic layer was separated. The solution was dried with magnesium sulfate, filtered and concentrated, and a light yellow oily substance was obtained. After purification in accordance with the column chromatography, a white solid substance was obtained. The obtained substance was washed with hexane twice and dried, and 1.97 g of Compound D-2 was obtained (the yield: 79%). The result of FD-MS on the obtained substance is shown in the following.

FD-MS: calcd.: $C_{48}H_{32}S_2Ge$ 745.54. found: 745

The obtained Compound D-2 was purified by sublimation at 320° C. under 7.7×10$^{-6}$ Torr and used for the vapor deposition. The purity was 99.8% in accordance with HPLC.

Synthesis Example 7

Synthesis of Compound A-7

Compound A-7 was synthesized in accordance with the route of synthesis shown in the following:

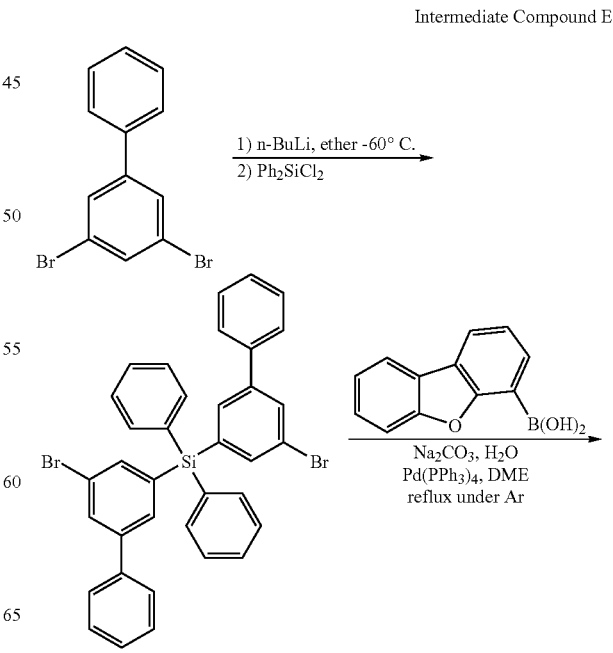

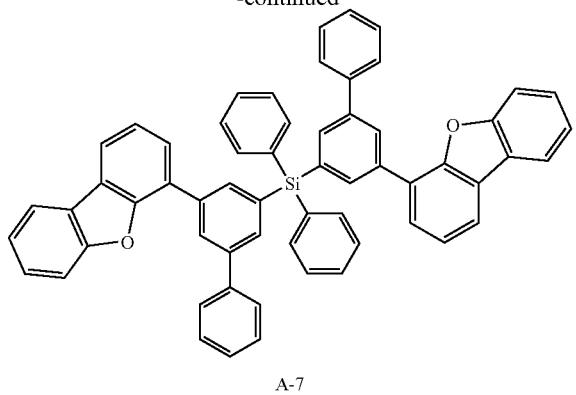

A-7

3,5-Dibromobiphenyl in an amount of 3.0 g was placed into a flask. Then, 40 ml of dehydrated diethyl ether was added under the atmosphere of argon, and 3,5-dibromobiphenyl was dissolved under stirring. The resultant solution was cooled at −70° C. in a MeOH-dry ice bath. To the cooled solution, 6.0 ml of a 1.6 M hexane solution of normal-butyllithium was added dropwise using a syringe. After the temperature was elevated at −10° C., the temperature was lowered at −40° C., and a solution prepared by dissolving 0.92 g of diphenyldichlorosilane into 10 ml of dehydrated diethyl ether was added dropwise. The temperature was elevated at 0° C. and, after it was confirmed in accordance with TLC that the reaction had been completed, the reaction was terminated by adding a saturated aqueous solution of ammonium chloride. After dichloromethane was added, the obtained mixture was washed with water, and the organic layer was separated. The solution was dried with magnesium sulfate, filtered and concentrated, and a yellow oily substance was obtained. After purification in accordance with the column chromatography, a white solid substance was obtained. The obtained substance was washed with hexane and dried, and 1.64 g of Intermediate Compound E was obtained (the yield: 58%). The result of FD-MS on the obtained substance is shown in the following.

FD-MS: calcd.: $C_{36}H_{26}Br_2Si$ 646.46. found: 646

Intermediate Compound E obtained above in an amount of 1.64 g, i.e., the entire amount, 1.07 g of 4-dibenzofuranboronic acid, 0.12 g of tetrakis-triphenylphosphinepalladium (0), 10 g of a 2M aqueous solution of sodium carbonate and 40 ml of dimethoxyethane were placed into a flask, and the resulting mixture was heated under the refluxing condition under the atmosphere of argon for 8 hours. After it was confirmed in accordance with TLC that the reaction had been completed, dichloromethane was added. The obtained mixture was washed with water and a saturated aqueous solution of sodium chloride, and the organic layer was separated. The solution was dried with magnesium sulfate, filtered and concentrated, and a yellow oily substance was obtained. After purification in accordance with the column chromatography, 1.87 g of Compound A-7 was obtained as a white solid substance (the yield: 90%). The result of FD-MS on the obtained substance is shown in the following.

FD-MS: calcd.: $C_{60}H_{40}SiO_2$ 821.04. found: 821

The obtained Compound A-7 was purified by sublimation at 350° C. under $6.1\times10^{-6}$ Torr and used for the vapor deposition. The purity was 99.3% in accordance with HPLC.

The apparatus and the conditions of the measurement in FD-MS in Synthesis Examples 1 to 7 are shown in the following.

<FD-MS>

Apparatus: HX110 (manufactured by NIPPON DENSHI Co., Ltd.)

Condition: The voltage of acceleration: 8 kV
  The range of scanning: m/z=50 to 1500

Type of the emitter: carbon

Current of the emitter: 0 mA→2 mA/minute→40 mA (kept for 10 minutes)

Example 1

Preparation of an Organic EL Device

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone under irradiation with ultraviolet light for 30 minutes. The cleaned glass substrate having the transparent electrode line was attached to a substrate holder of a vacuum vapor deposition apparatus. On the surface of the cleaned substrate at the side having the transparent electrode line, a film of HTM shown in the following having a thickness of 95 nm was formed in a manner such that the formed film covered the transparent electrode. The formed HTM film worked as the hole injecting and transporting layer. On the formed hole injecting and transporting film, a film of Compound A-2 obtained in Synthesis Example 1 as the host material and the above complex compound K-1 having a thickness of 30 nm was formed in accordance with the simultaneous vapor deposition by resistance heating. The concentration of the complex compound K-1 was 7% by weight. The formed film worked as the light emitting layer. Successively, a film of ETM1 shown in the following having a thickness of 25 nm was formed on the formed light emitting layer, and a film of ETM2 shown in the following having a thickness of 5 nm was laminated on the formed film of ETM1. The layer of ETM1 and the layer of ETM2 worked as the electron transporting layer and the electron injecting layer, respectively. Thereafter, a film of LiF having a thickness of 1 nm was formed as the electron injecting electrode (the cathode) at a rate of film formation of 1 Å/minute. On the formed layer of LiF, Al metal was vapor deposited to form a metal electrode having a thickness of 150 nm, and an organic EL device was prepared.

(Evaluation of the Light Emitting Property of the Organic EL Device)

In the test of passing the electric current, light was emitted from the organic EL device prepared as described above under driving with the direct electric current. The wavelength of the emitted light (λ), the luminance of the emitted light (L) and the current density (J) were measured, and the current efficiency (L/J) was obtained. The result is shown in Table 1. For the evaluation of the life, the time of period before the luminance was decreased to a half of the initial value of 1,500 cd/m² was measured, and the result is shown as the relative value using the result of Comparative Example 1 as the reference, which is set at 100.

HTM

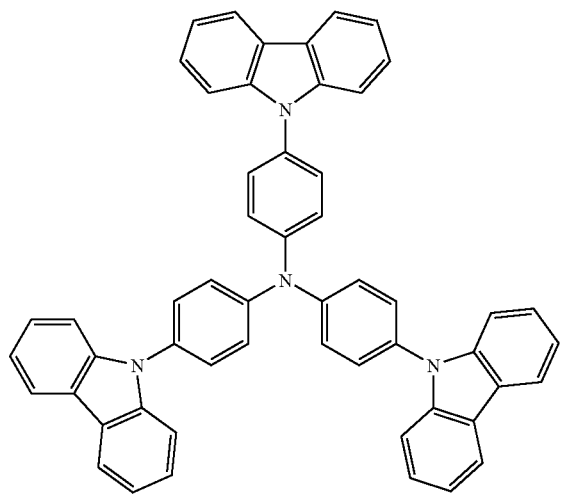

ETM2

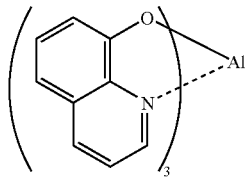

Examples 2 to 7

Organic EL devices were prepared in accordance with the same procedures as those conducted in Example 1 except that the host materials obtained in Synthesis Examples 2 to 7 were used in place of Compound A-2 as described in Table 1. The test of passing the electric current and the evaluation of the life were conducted in accordance with the same procedures as those conducted in Example 1. The results are shown in Table 1.

ETM1

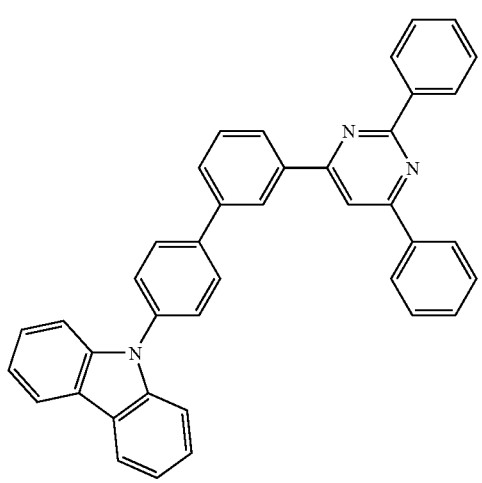

Comparative Example 1 to 4

Organic EL devices were prepared in accordance with the same procedures as those conducted in Example 1 except that the following Comparative Compounds 1 to 4, which are described in International Patent Application Laid-Open No. WO2004/095598 and Japanese Patent Application Laid-Open Nos. 2005-310672, 2005-306864 and 2005-317275, respectively, were used as the host materials in place of Compound A-2. The test of passing electric current and the evaluation of the life were conducted in accordance with the same procedures as those conducted in Example 1. The results are shown in Table 1.

TABLE 1

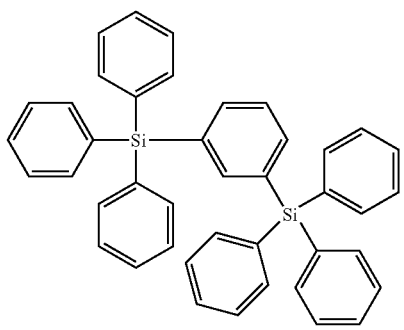

Comparative Compound 1

TABLE 1-continued

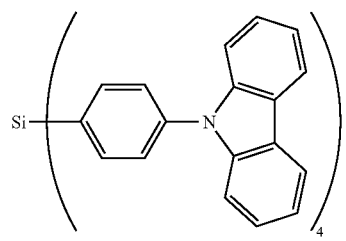

Comparative Compound 2

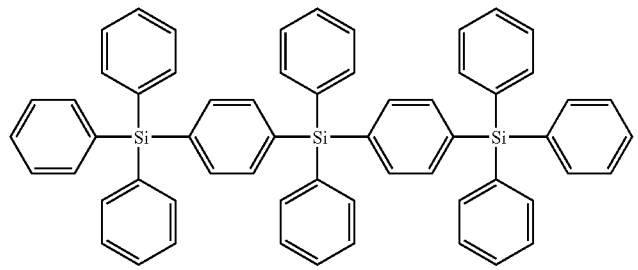

Comparative Compound 3

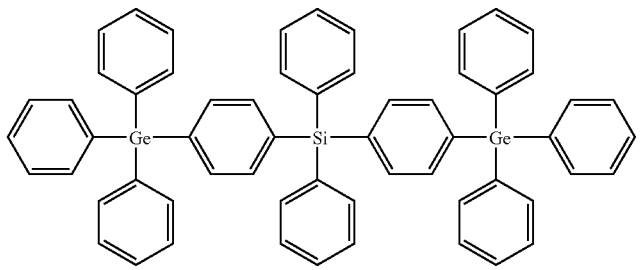

Comparative Compound 4

| | Host material | Luminance (cd/m²) | Voltage (V) | Current efficiency (cd/A) | Wavelength of emitted light (nm) | Life |
|---|---|---|---|---|---|---|
| Example 1 | A-2 | 112 | 6.4 | 28 | 483 | 261 |
| Example 2 | B-1 | 100 | 6.0 | 32 | 484 | 268 |
| Example 3 | B-2 | 102 | 5.8 | 29 | 483 | 327 |
| Example 4 | C-2 | 108 | 6.0 | 35 | 484 | 251 |
| Example 5 | C-7 | 110 | 6.4 | 38 | 483 | 330 |
| Example 6 | D-2 | 102 | 6.2 | 35 | 484 | 292 |
| Example 7 | A-7 | 110 | 6.4 | 32 | 484 | 284 |
| Comparative Example 1 | Comparative Compound 1 | 98 | 7.0 | 20 | 484 | 100 |
| Comparative Example 2 | Comparative Compound 2 | 102 | 6.4 | 24 | 484 | 147 |
| Comparative Example 3 | Comparative Compound 3 | 104 | 6.9 | 22 | 484 | 94 |
| Comparative Example 4 | Comparative Compound 4 | 100 | 7.0 | 21 | 484 | 67 |

As shown by the results in Table 1, the host materials used in Comparative Examples provided smaller current efficiencies, greater voltages and shorter lives than those provided by the host materials used in Examples.

INDUSTRIAL APPLICABILITY

As described specifically in the above, the organic EL device providing excellent efficiency of light emission, forming no defects in pixels, exhibiting excellent heat resistance and having a long life can be obtained by utilizing the material for organic EL devices comprising the compound represented by general formula (1) or (2) of the present invention.

Therefore, the organic EL device of the present invention is very useful as the light source for various electronic instruments.

The invention claimed is:

1. A material operable for organic electroluminescence devices which comprises a compound represented by general formula (2):

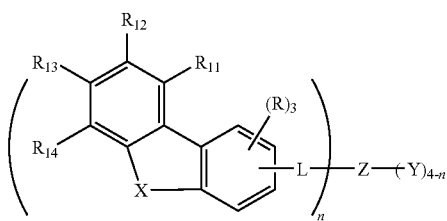

(2)

wherein
X represents a sulfur atom or an oxygen atom;
each of $R_{11}$ to $R_{14}$ and each R group is a hydrogen atom;
each L group is, independently, a phenylene group, a biphenylylene group, or a naphthylene group;
each Y group is, independently, a substituted or unsubstituted phenyl group, a substituted or unsubstituted biphenylyl group, or a substituted or unsubstituted naphthyl group;
Z represents a silicon atom or a germanium atom; and
n represents an integer of from 2 or 3.

2. A material according to claim 1, wherein a compound represented by formula (2) is a compound represented by one of general formulae (3) and (4):

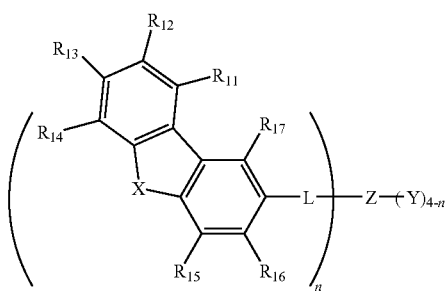

(3)

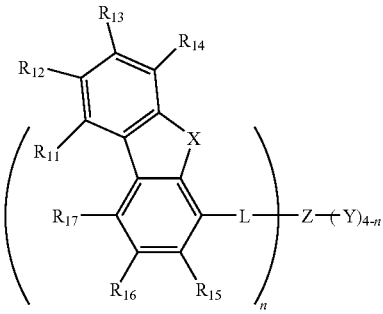

(4)

wherein $R_{11}$ to $R_{17}$ are as defined for $R_{11}$ to $R_{14}$ and R in general formula (2), and L, X, Z, Y and n are as defined in general formula (2).

3. An organic electroluminescence device which comprises a cathode, an anode and an organic thin film layer which comprises at least one layer comprising at least a light emitting layer and is disposed between the cathode and the anode, wherein at least one layer in the organic thin film layer comprises the material for organic electroluminescence devices described in claim 1.

4. An organic electroluminescence device according to claim 3, wherein the light emitting layer comprises the material operable for organic electroluminescence devices as a host material.

5. An organic electroluminescence device according to claim 3, wherein the light emitting layer comprises said material operable for an organic electroluminescence device as a host material and a phosphorescent light emitting material.

6. An organic electroluminescence device according to claim 3, wherein the light emitting layer comprises a host material and a phosphorescent light emitting material, and the phosphorescent light emitting material is a compound having a metal selected from the group consisting of iridium, osmium and platinum.

7. An organic electroluminescence device according to claim 3, wherein the light emitting layer comprises a host material and a phosphorescent light emitting material, and the phosphorescent light emitting material is a light emitting material having a metal-carbene carbon bond.

8. An organic electroluminescence device according to claim 3, wherein the light emitting layer comprises a metal complex compound emitting bluish light which exhibits a maximum luminance at a wavelength of 500 nm or smaller.

9. An organic electroluminescence device according to claim 3, which comprises an electron injecting layer disposed between the light emitting layer and the cathode, and the electron injecting layer comprises a cyclic derivative having nitrogen atom as a main component thereof.

10. An organic electroluminescence device according to claim 3, which comprises a hole transporting layer, and the hole transporting layer comprises the material for organic electroluminescence devices.

11. An organic electroluminescence device according to claim 3, which comprises at least one of an electron transporting layer and a hole barrier layer, and at least one of the electron transporting layer and the hole barrier layer comprises the material for organic electroluminescence devices.

12. An organic electroluminescence device according to claim 3, wherein a reducing dopant is added at an interfacial region between the cathode and the organic thin film layer.

13. A material according to claim 1, wherein the biphenylylene group is a para-bipheylene group, a meta-biphenylene group, or an ortho-biphenylene group.

14. A material according to claim 1, wherein n is 2.

15. A material according to claim 1, wherein n is 3.

16. A material operable for organic electroluminescence devices which comprises a compound represented by general formula (2):

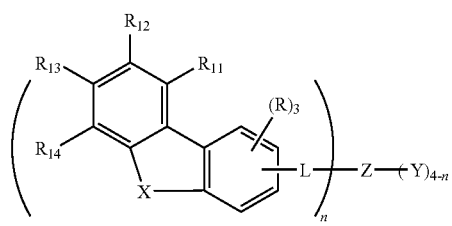

wherein
- $R_{11}$ to $R_{14}$ and R each independently represent a hydrogen atom;
- X represents a sulfur atom or an oxygen atom;
- each L group is, independently, a phenylene group, a biphenylene group, or a naphthylene group;
- each Y group is, independently, a phenylene group, a biphenylylene group, or a naphthylene group;
- Z is a germanium atom; and
- n represents an integer of from 2 or 3.

17. An organic electroluminescence device, which comprises a cathode, an anode and an organic thin film layer which comprises at least one layer comprising at least a light emitting layer and is disposed between the cathode and the anode, wherein at least one layer in the organic thin film layer comprises at least one member selected from the group consisting of

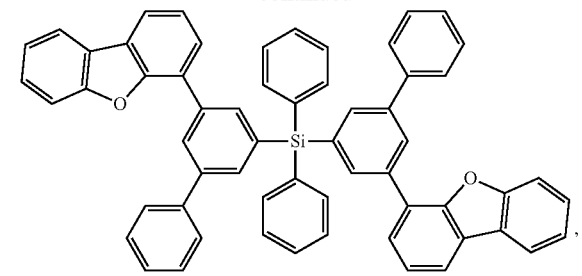

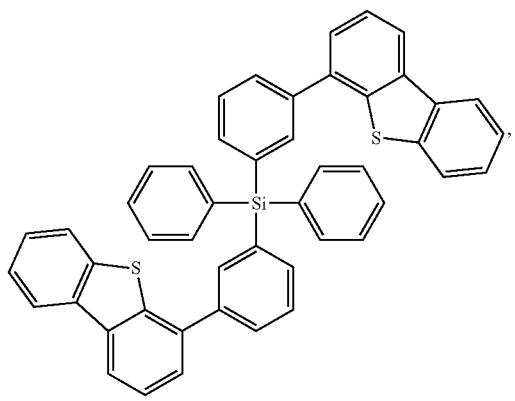

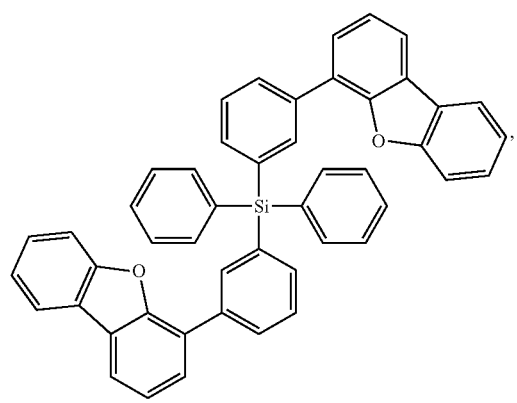

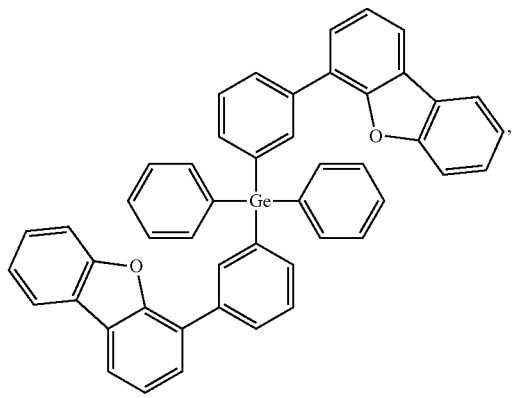

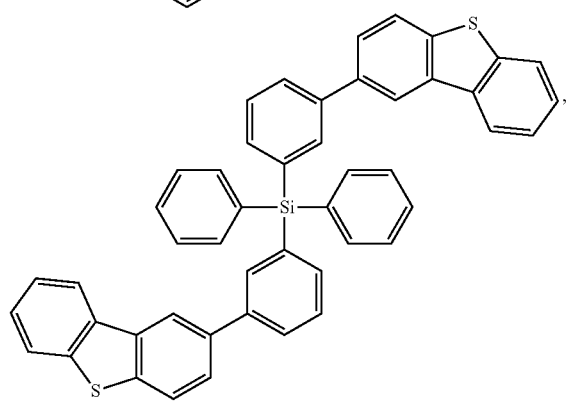

and

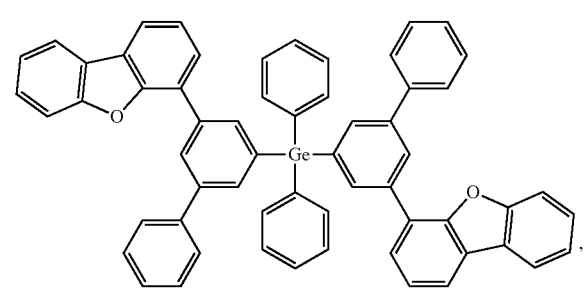

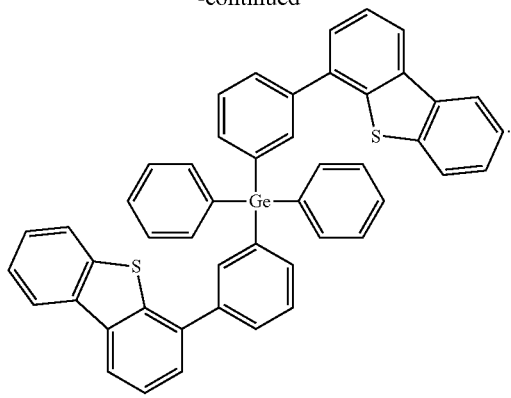

18. A material operable for organic electroluminescence devices which comprises a compound represented by general formula (2):

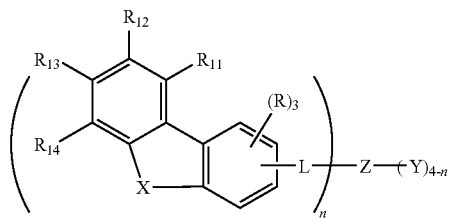

wherein
each of $R_{11}$ to $R_{14}$ and each R group is a hydrogen atom;
X represents a sulfur atom or an oxygen atom;
each L group is, independently, a phenylene group, a biphenylylene group, or a naphthylene group;
each Y group is, independently, a substituted or unsubstituted phenyl group, a substituted or unsubstituted biphenylyl group, or a substituted or unsubstituted naphthyl group;
Z represents a silicon atom; and
n represents an integer of from 2 or 3.

19. A material operable for organic electroluminescence devices which comprises a compound represented by general formula (2):

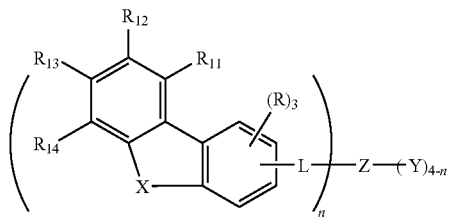

wherein
$R_{11}$ to $R_{14}$ and R each independently represent a hydrogen atom, an alkyl group having 1 to 10 carbon atoms, a heterocyclic group having 3 to 8 carbon atoms, an alkoxyl group having 1 to 10 carbon atoms, a non-condensed aryl group having 6 to 18 carbon atoms, a condensed aryl group having 6 to 12 carbon atoms, or an aryloxyl group having 6 to 18 carbon atoms;
X represents a sulfur atom or an oxygen atom;
L represents an alkylene group having 1 to 10 carbon atoms which may have substituents, a non-condensed arylene group having 6 to 40 carbon atoms which may have substituents, a condensed arylene group having 6 to 12 carbon atoms which may have substituents or a divalent aromatic heterocyclic group having 3 to 40 carbon atoms which may have substituents;
Y represents a methyl group, an ethyl group, a propyl group, an isopropyl group, an n-butyl group, an s-butyl group, an isobutyl group, a t-butyl group, a substituted or unsubstituted phenyl group, a substituted or unsubstituted naphthyl group, a substituted or unsubstituted biphenylyl group, a substituted or unsubstituted terphenylyl group, and, when a plurality of groups represented by Y are present, Y may represent a same group or different groups;
Z represents a silicon atom or a germanium atom; and
n represents an integer of from 2 or 3.

* * * * *